United States Patent
Usui et al.

(10) Patent No.: US 7,683,069 B2
(45) Date of Patent: *Mar. 23, 2010

(54) 3-SUBSTITUTED-4-PYRIMIDONE DERIVATIVES

(75) Inventors: Yoshihiro Usui, Tokyo (JP); Masahiro Okuyama, Tokyo (JP); Tokushi Hanano, Tokyo (JP)

(73) Assignees: Mitsubishi Tanabe Pharma Corporation, Osaka (JP); Sanofi-Aventis, Paris (FR)

( * ) Notice: Subject to any disclaimer, the term of this patent is extended or adjusted under 35 U.S.C. 154(b) by 789 days.

This patent is subject to a terminal disclaimer.

(21) Appl. No.: 10/538,766

(22) PCT Filed: Dec. 12, 2003

(86) PCT No.: PCT/JP03/15968

§ 371 (c)(1),
(2), (4) Date: Nov. 20, 2006

(87) PCT Pub. No.: WO2004/055007

PCT Pub. Date: Jul. 1, 2004

(65) Prior Publication Data
US 2007/0142409 A1    Jun. 21, 2007

(30) Foreign Application Priority Data
Dec. 16, 2002 (JP) ............................. 2002-383300
Dec. 16, 2002 (JP) ............................. 2002-383301

(51) Int. Cl.
C07D 401/14    (2006.01)
A61K 31/505    (2006.01)

(52) U.S. Cl. ................ 514/256; 514/272; 544/296; 544/320; 544/321

(58) Field of Classification Search ............... 544/296, 544/320, 321; 514/256, 272
See application file for complete search history.

(56) References Cited

U.S. PATENT DOCUMENTS

| | | | |
|---|---|---|---|
| 4,166,180 A | 8/1979 | Kato et al. | |
| 4,507,302 A | 3/1985 | Fast et al. | |
| 4,619,933 A | 10/1986 | Stringfellow et al. | |
| 4,725,600 A | 2/1988 | Takaya et al. | |
| 5,612,286 A | 3/1997 | Mayer et al. | |
| 6,096,753 A | 8/2000 | Spohr et al. | |
| 6,107,301 A | 8/2000 | Aldrich et al. | |
| 6,410,729 B1 | 6/2002 | Spohr et al. | |
| 6,420,385 B1 | 7/2002 | Spohr et al. | |
| 6,586,441 B2 | 7/2003 | Borroni et al. | |
| 6,844,335 B2 | 1/2005 | Almario Garcia et al. | |
| 7,504,411 B2 * | 3/2009 | Watanabe et al. | 514/273 |
| 2003/0187004 A1 | 10/2003 | Almario Garcia et al. | |
| 2005/0090490 A1 | 4/2005 | Uehara et al. | |
| 2005/0130967 A1 | 6/2005 | Uehara et al. | |
| 2005/0130998 A1 | 6/2005 | Almario Carcia et al. | |
| 2006/0252768 A1 | 11/2006 | Watanabe et al. | |

FOREIGN PATENT DOCUMENTS

| | | |
|---|---|---|
| EP | 0168262 | 1/1986 |
| EP | 0354179 | 7/1989 |
| EP | 1136482 | 9/2001 |
| HU | 218974 | 8/1995 |
| HU | P0001698 | 4/2001 |
| JP | 49-035631 | 4/1974 |
| JP | 49-35632 | 4/1974 |
| JP | 49-035633 | 4/1974 |
| JP | 49-35634 | 4/1974 |
| JP | 49-35631 | 9/1974 |
| JP | 49-35632 | 9/1974 |
| JP | 49-35633 | 9/1974 |
| JP | 49-35634 | 9/1974 |
| JP | 52-071481 | 6/1977 |
| JP | 52-139085 | 11/1977 |
| JP | 6-239893 | 8/1994 |
| JP | 6-329551 | 11/1994 |
| WO | 93/11231 | 6/1998 |
| WO | 98/24780 | 6/1998 |

(Continued)

OTHER PUBLICATIONS

Tomizawa et al., Tau-tubulin kinase phosphorylates tau at Ser-208 and Ser-210, sites found in paired helical filament-tau, FEBS Letters, 492, pp. 221-227, 2001.*

(Continued)

*Primary Examiner*—Deepak Rao
(74) *Attorney, Agent, or Firm*—Greenblum & Bernstein, P.L.C.

(57) ABSTRACT

A pyrimidone derivative represented by formula (I) or a salt thereof, or a solvate thereof or a hydrate thereof useful as a tau protein kinase 1 inhibitor: wherein X represents CH or nitrogen atom; $R_1$ represents a $C_1$-$C_{12}$ alkyl group which may be substituted; $R_2$ represents a $C_1$-$C_8$ alkyl group which may be substituted, a benzene ring which may be substituted, a naphthalene ring which may be substituted, an indan ring which may be substituted, a tetrahydronaphthalene ring which may be substituted, or an optionally substituted heterocyclic ring having 1 to 4 hetero atoms selected from the group consisting of oxygen atom, sulfur atom, and nitrogen atom, and having 5 to 10 ring-constituting atoms in total.

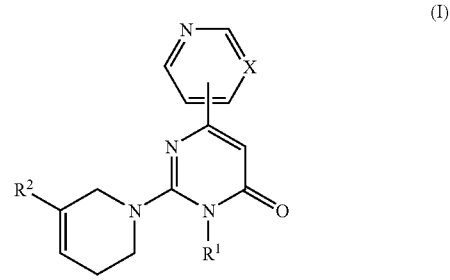

(I)

7 Claims, No Drawings

FOREIGN PATENT DOCUMENTS

| | | |
|---|---|---|
| WO | 98/24782 | 6/1998 |
| WO | 00/18758 | 4/2000 |
| WO | 01/70728 | 9/2001 |
| WO | 01/70729 | 9/2001 |
| WO | 03/027080 | 9/2002 |
| WO | 03/037888 | 5/2003 |
| WO | 2004/085408 | 10/2004 |

OTHER PUBLICATIONS

Simone, Oncology: Introduction, Cecil Textbook of Medicine, 20th Edition, vol. 1, pp. 1004-1010, 1996.*
Damasio, Alzheimer's Disease and Related Dementias, Cecil Textbook of Medicine, 20th Edition, vol. 2, pp. 1992-1996, 1996.*
Layzer, Degenerative Diseases of the Nervous system, Cecil Textbook of Medicine, 20th Edition, vol. 2, pp. 2050-2057, 1996.*
Chemical Abstract No. 83:10129 of JP 49-35634 (1974).
English translation of Japanese Kokoku JP 49-35632 (1974).
H. Yinglin, Tetrahedron Letters, vol. 30, No. 39, 1989, pp. 5285-5286.
English language Abstract of JP 6-329551 Date Publication Nov. 29, 2004.
H. Yinglin, Synthesis, pp. 122-124, Feb. 1990.
R.L. Duncan Jr. et al., J. Med. Chem., vol. 13, No. 1, Jan. 1970, pp. 1-6.
D.L. Thai et al., J. Med. Chem., vol. 41, 1998, pp. 591-601.
Chemical Abstracts, vol. 100, No. 28, 1984, Columbus, Ohio, US, Abstract No. 174768e, M.F. Brana et al., "Reaction of N-(1-Oxido-4-Pyridylmethyl)-3,5-Dimethylbenzamide with Malononitrile in Acetic Anhydride", p. 627; XP002127059.
Chemical Abstracts, vol. 84, No. 7, 1976, Columbus, Ohio, US, Abstract No. 44112b, Tani et al., "4-Hydroxy-Pyridylpyrimidine Derivatives", p. 502, XP002127060.
Chemical Abstracts, vol. 82, No. 28, 1975, Columbus, Ohio, US, Abstract No. 171028n, Tani et al., "2,4,5-Trisubstituted-6-Pyridylpyrimidine Derivatives", p. 555, XP002127061.
Chemical Abstracts, vol. 83, No. 28, 1975, Columbus, Ohio, US, Abstract No. 10127z, Tani et al., "5-Nitro-6-Pyridylpyrimidine Derivatives", p. 853, XP002127062.
Chemical Abstract 1992, vol. 116, Abstract # 59167.
Chemical Abtract 1966, vol. 65, Abstact # 90645.
Von Hans-Joachim Kabbe, "Substituierte 4-Hydroxy- und 4-Amino-Pyrimidine", Liebigs. Ann. Chem., vol. 701, pp. 144-149 (1967).
Harvey I. Skulnick et al., "Pyrimidinones. 1. 2-Amino-5-Halo-6-Arly-4(3H)-Pyrimidinones. Interferon-Inducing Antiviral Agents", J. Med. Chem., vol. 28, pp. 1864-1869 (1985).

U.S. Appl. No. 09/787,426, filed Jul. 2, 2001 to Watanabe et al.
English language Abstract of JP 52-071481, published Jun. 14, 1977.
Anthony R. West, Solid State Chemistry and Its Applications, Wiley, New York, 1988 pp. 358 and 365.
Sudha R. Vippagunta et al., "Crystalline Solids", Advance Drug Delivery Reviews, vol. 48, pp. 3-26 (2001).
Tani et al., CAPLUS Abstract 84:44112 (1976).
Joachim Ulrich, Chapter 4: Crystallization, Krik-Othmer Encyclopedia of Chemical Technology (Aug. 2002).
G. Glenner et al., Biochemical and Biophysical Research Communications, vol. 120, No. 3, 1984, pp. 885-890.
C.L. Masters et al., The EMBO Journal, vol. 4, No. 11, 1985, pp. 2757-2763.
C.L. Masters et al., Proc. Natl. Acad. Sci. USA, vol. 82, Jun. 1985, pp. 4245-4249.
C.M. Wischik et al., Proc. Natl. Acad. Sci. USA, vol. 85, Jun. 1988, pp. 4506-4510.
J. Kondo et al., Neuron, vol. 1, Nov. 1988, pp. 827-834.
R. Sherrington et al., Nature, vol. 375, Jun. 29, 1995, pp. 754-760.
E. Levy-Lahad et al., Science, vol. 269, Aug. 18, 1995, pp. 973-977.
E.I. Rogaev et al., Nature, vol. 376, Aug. 31, 1995, pp. 775-778.
D.R. Borchelt et al., Neuron, vol. 17, Nov. 1996, pp. 1005-1013.
T. Tomita et al., Proc. Natl. Acad. Sci. USA, vol. 94, Mar. 1997, pp. 2025-2030.
Sai-Shin Igaku, vol. 49, No. 9, 1994, pp. 1506-1512.
D.W. Dickson et al., Society for Neuroscience Abstracts, vol. 17, 1991, pp. 1445.
R. Siman et al., The Journal of Neuroscience, vol. 10, No. 7, Jul. 1990, pp. 2400-2411.
Shin-kei Shinpo, vol. 34, 1990, pp. 343-349.
Tanpaku-shitu Kaku-san Koso, vol. 41, 1996, pp. 1476-1483.
Tanpaku-shitu Kaku-san Koso, vol. 36, 1991, pp. 2-11.
Igaku no Ayumi, vol. 158, No. 9, Aug. 31, 1991, pp. 511-514.
Y. Ihara et al., J. Biochem., vol. 99, 1986, pp. 1807-1810.
I. Grundke-Iqbal et al., Proc. Natl. Acad. Sci. USA, vol. 83, Jul. 1986, pp. 4913-4917.
Seikagaku, vol. 64, No. 5, pp. 308-312, 1992.
K. Ishiguro et al., J. Biol. Chem., vol. 267, No. 15, May 25, 1992, pp. 10897-10901.
K. Ishiguro et al., FEBS Lett., vol. 325, Jul. 1993, pp. 167-172.
English Language Abstract of JP 6-239893, Date Publication Aug. 30, 1994.
B.A. Yankner et al., Science, vol. 250, 1990, pp. 279-283.
A. Takashima et al., Proc. Natl. Acad. Sci. USA, vol. 90, Aug. 1993, pp. 7789-7793.

* cited by examiner

3-SUBSTITUTED-4-PYRIMIDONE DERIVATIVES

This application is a 371 of PCT/JP03/15968 filed Dec. 12, 2003.

TECHNICAL FIELD

The present invention relates to compounds that are useful as an active ingredient of a medicament for preventive and/or therapeutic treatment of diseases mainly caused by abnormal activity of tau protein kinase 1, such as neurodegenerative diseases (e.g. Alzheimer disease).

BACKGROUND ART

Alzheimer disease is progressive senile dementia, in which marked cerebral cortical atrophy is observed due to degeneration of nerve cells and decrease of nerve cell number. Pathologically, numerous senile plaques and neurofibrillary tangles are observed in brain. The number of patients has been increased with the increment of aged population, and the disease arises a serious social problem. Although various theories have been proposed, a cause of the disease has not yet been elucidated. Early resolution of the cause has been desired.

It has been known that the degree of appearance of two characteristic pathological changes of Alzheimer disease well correlates to the degree of intellectual dysfunction. Therefore, researches have been conducted from early 1980's to reveal the cause of the disease through molecular level investigations of components of the two pathological changes. Senile plaques accumulate extracellularly, and β amyloid protein has been elucidated as their main component (abbreviated as "Aβ" hereinafter in the specification: Biochem. Biophys. Res. Commun., 120, 885 (1984); EMBO J., 4, 2757 (1985); Proc. Natl. Acad. Sci. USA, 82, 4245 (1985)). In the other pathological change, i.e., the neurofibrillary tangles, a double-helical filamentous substance called paired helical filament (abbreviated as "PHF" hereinafter in the specification) accumulate intracellularly, and tau protein, which is a kind of microtubule-associated protein specific for brain, has been revealed as its main component (Proc. Natl. Acad. Sci. USA, 85, 4506 (1988); Neuron, 1, 827 (1988)).

Furthermore, on the basis of genetic investigations, presenilins 1 and 2 were found as causative genes of familial Alzheimer disease (Nature, 375, 754 (1995); Science, 269, 973 (1995); Nature. 376, 775 (1995)), and it has been revealed that presence of mutants of presenilins 1 and 2 promotes the secretion of Aβ (Neuron, 17, 1005 (1996); Proc. Natl. Acad. Sci. USA, 94, 2025 (1997)). From these results, it is considered that, in Alzheimer disease, Aβ abnormally accumulates and agglomerates due to a certain reason, which engages with the formation of PHF to cause death of nerve cells. It is also expected that extracellular outflow of glutamic acid and activation of glutamate receptor responding to the outflow may possibly be important factors in an early process of the nerve cell death caused by ischemic cerebrovascular accidents (Saishin Igaku [Latest Medicine], 49, 1506 (1994)).

It has been reported that kainic acid treatment that stimulates the AMPA receptor, one of glutamate receptor, increases mRNA of the amyloid precursor protein (abbreviated as "APP" hereinafter in the specification) as a precursor of Aβ (Society for Neuroscience Abstracts, 17, 1445 (1991)), and also promotes metabolism of APP (The Journal of Neuroscience, 10, 2400 (1990)). Therefore, it has been strongly suggested that the accumulation of Aβ is involved in cellular death due to ischemic cerebrovascular disorders. Other diseases in which abnormal accumulation and agglomeration of Aβ are observed include, for example, Down syndrome, cerebral bleeding due to solitary cerebral amyloid angiopathy, Lewy body disease (Shin-kei Shinpo [Nerve Advance], 34, 343 (1990); Tanpaku-shitu Kaku-san Koso [Protein, Nucleic Acid, Enzyme], 41, 1476 (1996)) and the like. Furthermore, as diseases showing neurofibrillary tangles due to the PHF accumulation, examples include progressive supranuclear palsy, subacute sclerosing panencephalitic parkinsonism, postencephalitic parkinsonism, pugilistic encephalitis, Guam parkinsonism-dementia complex, Lewy body disease and the like (Tanpakushitu Kakusan Koso [Protein, Nucleic Acid, Enzyme], 36, 2 (1991); Igaku no Ayumi [Progress of Medicine], 158, 511 (1991); Tanpakushitu Kakusan Koso [Protein, Nucleic Acid, Enzyme], 41, 1476 (1996)).

The tau protein is generally composed of a group of related proteins that forms several bands at molecular weights of 48-65 kDa in SDS-polyacrylamide gel electrophoresis, and it promotes the formation of microtubules. It has been verified that tau protein incorporated in the PHF in the brain suffering from Alzheimer disease is abnormally phosphorylated compared with usual tau protein (J. Biochem., 99, 1807 (1986); Proc. Natl. Acad. Sci. USA, 83, 4913 (1986)). An enzyme catalyzing the abnormal phosphorylation has been isolated. The protein was named as tau protein kinase 1 (abbreviated as "TPK1" hereinafter in the specification), and its physicochemical properties have been elucidated (Seikagaku [Biochemistry], 64, 308 (1992); J. Biol. Chem., 267, 10897 (1992)). Moreover, cDNA of rat TPK1 was cloned from a rat cerebral cortex cDNA library based on a partial amino acid sequence of TPK1, and its nucleotide sequence was determined and an amino acid sequence was deduced (Japanese Patent Un-examined Publication [Kokai] No. 6-239893/1994). As a result, it has been revealed that the primary structure of the rat TPK1 corresponds to that of the enzyme known as rat GSK-3β (glycogen synthase kinase 3β, FEBS Lett., 325, 167 (1993)).

It has been reported that Aβ, the main component of senile plaques, is neurotoxic (Science, 250, 279 (1990)). However, various theories have been proposed as for the reason why Aβ causes the cell death, and any authentic theory has not yet been established. Takashima et al. observed that the cell death was caused by Aβ treatment of fetal rat hippocampus primary culture system, and then found that the TPK1 activity was increased by Aβ treatment and the cell death by Aβ was inhibited by antisense of TPK1 (Proc. Natl. Acad. Sci. USA, 90, 7789 (1993); Japanese Patent Un-examined Publication [Kokai] No. 6-329551/1994).

In view of the foregoing, compounds which inhibit the TPK1 activity may possibly suppress the neurotoxicity of Aβ and the formation of PHF and inhibit the nerve cell death in the Alzheimer disease, thereby cease or defer the progress of the disease. The compounds may also be possibly used as a medicament for therapeutic treatment of neurodegenerative diseases such as cerebrovascular accidents (e.g. ischemic, age-related macular degeneration), Down syndrome, cerebral bleeding due to cerebral amyloid angiopathy, Parkinson's disease, subacute sclerosing panencephalitic parkinsonism, postencephalitic parkinsonism, pugilistic encephalitis, Guam parkinsonism-dementia complex, Lewy body disease, tauopathies (e.g. Pick's disease, corticobasal degeneration, frontotemporal dementia, progressive supranuclear palsy), and other dementia including vascular dementia; acute and other traumatic injuries, brain and spinal cord trauma, peripheral neuropathies, retinopathies and glaucoma, as well as other diseases such as non-insulin dependent diabetes (such as diabetes type II), obesity, manic depressive illness, schizophrenia, alopecia, cancers such as breast cancer, non-small cell lung carcinoma, thyroid cancer, T or B-cell leukemia, and several virus-induced tumors.

As structurally similar compounds to the compounds of the present invention represented by formula (I) described later, compounds represented by the following formula (A) are known:

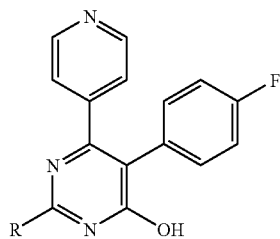

(A)

wherein R represents 2,6-dichlorobenzyl group, 2-(2-chlorophenyl)ethylamino group, 3-phenylpropylamino group, or 1-methyl-3-phenylpropylamino group (WO98/24782). The compounds represented by formula (A) are characterized to have 4-fluorophenyl group at the 5-position of the pyrimidine ring and a hydroxy group at the 4-position, and not falling within the scope of the present invention. Moreover, main pharmacological activity of the compounds represented by formula (A) is anti-inflammatory effect, whereas the compounds of the present invention represented by formula (I) are useful as a TPK1 inhibitor or a medicament for therapeutic treatment of neurodegenerative diseases, and therefore, their pharmacological activities are totally different to each other.

Patent Document 1: WO 00/18758

Patent Document 2: WO 01/70728

Patent Document 3 WO 01/70729

DISCLOSURE OF THE INVENTION

An object of the present invention is to provide compounds useful as an active ingredient of a medicament for preventive and/or therapeutic treatment of diseases such as Alzheimer disease. More specifically, the object is to provide novel compounds useful as an active ingredient of a medicament that enables radical prevention and/or treatment of the neurodegenerative diseases such as Alzheimer disease by inhibiting the TPK1 activity to suppress the neurotoxicity of Aβ and the formation of the PHF and by inhibiting the death of nerve cells.

In order to achieve the foregoing object, the inventors of the present invention conducted screenings of various compounds having inhibitory activity against the phosphorylation of TPK1. As a result, they found that compounds represented by the following formula (I) had the desired activity and were useful as an active ingredient of a medicament for preventive and/or therapeutic treatment of the aforementioned diseases. The present invention was achieved on the basis of these findings.

The present invention thus provides 3-substituted-4-pyrimidone derivatives represented by formula (I) or salts thereof, or solvates thereof or hydrates thereof:

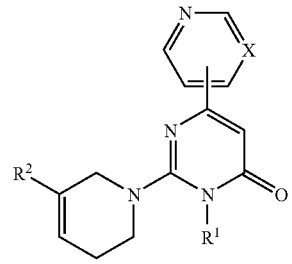

(I)

wherein X represents CH or nitrogen atom;

$R^1$ represents a $C_1$-$C_{12}$ alkyl group which may be substituted;

$R^2$ represents a $C_1$-$C_8$ alkyl group which may be substituted, a benzene ring which may be substituted, a naphthalene ring which may be substituted, an indan ring which may be substituted, a tetrahydronaphthalene ring which may be substituted, or an optionally substituted heterocyclic ring having 1 to 4 hetero atoms selected from the group consisting of oxygen atom, sulfur atom, and nitrogen atom, and having 5 to 10 ring-constituting atoms in total.

According to another aspect of the present invention, there is provided a medicament comprising as an active ingredient a substance selected from the group consisting of the 3-substituted-4-pyrimidone derivative represented by formula (1) and the physiologically acceptable salt thereof, and the solvate thereof and the hydrate thereof. As preferred embodiments of the medicament, there are provided the aforementioned medicament which is used for preventive and/or therapeutic treatment of diseases caused by tau protein kinase 1 hyperactivity, and the aforementioned medicament which is used for preventive and/or therapeutic treatment of neurodegenerative diseases. As further preferred embodiments of the present invention, there are provided the aforementioned medicament wherein the disease is selected from the group consisting of Alzheimer disease, cerebrovascular accidents (e.g. ischemic, age-related macular degeneration), Down syndrome, cerebral bleeding due to cerebral amyloid angiopathy, Parkinson's disease, subacute sclerosing panencephalitic parkinsonism, postencephalitic parkinsonism, pugilistic encephalitis, Guam parkinsonism-dementia complex, Lewy body disease, tauopathies (e.g. Pick's disease, corticobasal degeneration, frontotemporal dementia, progressive supranuclear palsy), and other dementia including vascular dementia; acute and other traumatic injuries, brain and spinal cord trauma, peripheral neuropathies, retinopathies and glaucoma, as well as other diseases such as non-insulin dependent diabetes (such as diabetes type II), obesity, manic depressive illness, schizophrenia, alopecia, cancers such as breast cancer, non-small cell lung carcinoma, thyroid cancer, T or B-cell leukemia, and several virus-induced tumors; and the aforementioned medicament in the form of pharmaceutical composition containing the above substance as an active ingredient together with one or more pharmaceutical additives. The present invention further provides an inhibitor of tau protein kinase 1 comprising as an active ingredient a substance selected from the group consisting of the 3-substituted-4-pyrimidone derivative of formula (I) and the salt thereof, and the solvate thereof and the hydrate thereof.

According to further aspects of the present invention, there are provided a method for preventive and/or therapeutic treatment of a disease caused by tau protein kinase 1 hyperactivity, which comprises the step of administering to a patient a preventively and/or therapeutically effective amount of a substance selected from the group consisting of the 3-substituted-4-pyrimidone derivative of formula (I) and the physiologically acceptable salt thereof, and the solvate thereof and the hydrate thereof and a use of a substance selected from the group consisting of the 3-substituted-4-pyrimidone derivative of formula (I) and the physiologically acceptable salt thereof, and the solvate thereof and the hydrate thereof for the manufacture of the aforementioned medicament.

BEST MODE FOR CARRYING OUT THE INVENTION

The alkyl group used herein may be either linear or branched. The $C_1$-$C_{12}$ alkyl group represented by $R^1$ may be, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, or a linear or branched heptyl group, octyl group, nonyl group, decyl group, undecyl group or dodecyl group. In the specification, when a functional group is defined as "which may be substituted" or "optionally substituted", the number of substituents as well as their types and substituting positions are not particularly limited, and when two or more substituents are present, they may be the same or different.

When the $C_1$-$C_{12}$ alkyl group represented by $R^1$ has one or more substituents, the alkyl group may have one or more substituents selected from the group consisting of a halogen atom; a cyano group; a hydroxyl group; a nitro group; a $C_1$-$C_5$ alkoxyl group such as methoxy group, ethoxy group, propoxy group, isopropoxy group, butoxy group, isobutoxy group, tert-butoxy group; an amino group, $C_1$-$C_3$ alkylamino group or $C_2$-$C_6$ dialkylamino group; a $C_6$-$C_{10}$ aryl group such as phenyl group, 1-naphthyl group, and 2-naphthyl group.

The $C_1$-$C_8$ alkyl group represented by $R^2$ may be, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, or a linear or branched heptyl group or octyl group.

When the $C_1$-$C_8$ alkyl group represented by $R^2$ has one or more substituents, the alkyl group may have one or more substituents selected from the groups consisting of a halogen atom, a $C_1$-$C_6$ alkoxyl group, a $C_3$-$C_8$ cycloalkyl group, a benzene ring which may be substituted, a naphthalene ring which may be substituted, phenoxy group which may be substituted or phenylamino group which may be substituted.

When the benzene ring, the naphthalene ring, the phenoxy group, the phenylamino group are substituents of the $C_1$-$C_8$ alkyl group represented by $R^2$, mentioned here above, they may have one or more substituents selected from the group consisting of a $C_1$-$C_5$ alkyl group such as methyl group, ethyl group, propyl group, isopropyl group, butyl group, isobutyl group, sec-butyl group, tert-butyl group, pentyl group, isopentyl group, neopentyl group, 1,1-dimethylpropyl group; a $C_3$-$C_6$ cycloalkyl group such as cyclopropyl group, cyclobutyl group, cyclopentyl group, cyclohexyl group; a $C_1$-$C_5$ alkoxyl group such as methoxy group, ethoxy group, propoxy group, isopropoxy group, butoxy group, isobutoxy group, tert-butoxy group, pentyloxy group, and isopentyloxy group; a $C_1$-$C_5$ alkylthio group such as methylthio group, ethylthio group, propylthio group, butylthio group, and pentylthio group; a halogen atom such as fluorine atom, chlorine atom, bromine atom, and iodine atom; a $C_1$-$C_5$ halogenated alkyl group such as trifluoromethyl group; hydroxyl group; cyano group; amino group.

When the benzene ring, the naphthalene ring, the indan ring, the tetrahydronaphthalene ring or the heterocyclic ring represented by $R^2$ has one or more substituents, the rings may have one or more substituents selected from the group consisting of a $C_1$-$C_5$ alkyl group such as methyl group, ethyl group, propyl group, isopropyl group, butyl group, isobutyl group, sec-butyl group, tert-butyl group, pentyl group, isopentyl group, neopentyl group, 1,1-dimethylpropyl group; a $C_3$-$C_6$ cycloalkyl group such as cyclopropyl group, cyclobutyl group, cyclopentyl group, cyclohexyl group; a $C_3$-$C_6$ cycloalkyloxy group such as cyclopropyloxy group, cyclobutyloxy group, cyclopentyloxy group, cyclohexyloxy group; hydroxy group; a $C_1$-$C_8$ alkoxyl group such as methoxy group, ethoxy group, propoxy group, isopropoxy group, butoxy group, isobutoxy group, tert-butoxy group, pentyloxy group, and isopentyloxy group; a $C_4$-$C_7$ cycloalkylalkoxyl group such as cyclopropylmethoxy group, cyclopentylmethoxy group; a $C_1$-$C_5$ alkylthio group such as methylthio group, ethylthio group, propylthio group, butylthio group, and pentylthio group; a $C_1$-$C_5$ alkylsulfonyl group such as methanesulfonyl group, ethanesulfonyl group, propanesulfonyl group, butanesulfonyl group, and pentanesulfonyl group; a halogen atom such as fluorine atom, chlorine atom, bromine atom, and iodine atom; a $C_1$-$C_5$ halogenated alkyl group such as trifluoromethyl group; a $C_1$-$C_5$ halogenated alkoxyl group such as trifluoromethoxy group, 2,2,2-trifluoroethoxy group; cyano group; nitro group; formyl group; a $C_2$-$C_6$ alkylcarbonyl group such as acetyl group, propionyl group, butyryl group, and valeryl group; a benzene ring, a naphthalene ring, phenoxy group or phenylamino group; amino group; a $C_1$-$C_5$ monoalkylamino group such as methylamino group, ethylamino group, propylamino group, isopropylamino group, butylamino group, isobutylamino group, tert-butylamino group, pentylamino group, and isopentylamino group; a $C_2$-$C_{10}$ dialkylamino group such as dimethylamino group, ethylmethylamino group, diethylamino group, methylpropylamino group, and diisopropylamino group; a $C_2$-$C_{10}$ monoaklaminomethyl group such as methylaminomethyl group, ethylaminomethyl group, propylaminomethyl group, isoproylaminomethyl group, butylaminomethyl group, isobutylaminomethyl group, tert-butylaminomethyl group, pentylaminomethyl group, isopentylaminomethyl; a $C_3$-$C_{11}$ dialkylaminomethyl group such as dimethylaminomethyl group, diethylaminomethyl group, ethylmethylaminomethyl group, methylpropylaminomethyl group; pyrrolidinylmethyl group; piperidinylmethyl group; morpholinomethyl group; piperazinylmethyl group; pyrrolylmethyl group; imidazolylmethyl group; pyrazolylmethyl group; triazolylmethyl group; and pyrrolidinylcarbonyl group. The above explained substituents may further be substituted with one or more other substituents which may preferably be chosen from the groups as exemplified above.

The heterocyclic ring having 1 to 4 hetero atoms selected from the group consisting of oxygen atom, sulfur atom, and nitrogen atom, and having 5 to 10 ring-constituting atoms represented by $R^2$ may be, for example, furan ring, dihydrofuran ring, tetrahydrofuran ring, pyran ring, dihydropyran ring, tetrahydropyran ring, benzofuran ring, dihydrobenzofuran, isobenzofuran ring, chromene ring, chroman ring, isochroman ring, thiophene ring, benzothiophene ring, pyrrole ring, pyrroline ring, pyrrolidine ring, imidazole ring, imidazoline ring, imidazolidine ring, pyrazole ring, pyrazoline ring, pyrazolidine ring, triazole ring, tetrazole ring, pyridine ring, pyridine oxide ring, piperidine ring, pyrazine ring, piperazine ring, pyrimidine ring, pyridazine ring, indole ring, indoline ring, isoindole ring, isoindoline ring, indazole ring, benzimidazole ring, benzotriazole ring, benzisoxazole ring, 1H-indazole ring, tetrahydroisoquinoline ring, benzothiazolinone ring, benzoxazolinone ring, purine ring, quinolizine ring, quinoline ring, phthalazine ring, naphthyridine ring, quinoxaline ring, quinazoline ring, cinnoline ring, pteridine ring, oxazole ring, oxazolidine ring, isoxazole ring, isoxazolidine ring, oxadiazole ring, thiazole ring, benzothiazole ring, thiazylidine ring, isothiazole ring, isothiazolidine ring, benzodioxole ring, dioxane ring, benzodioxane ring, dithian ring, morpholine ring, thiomorpholine ring, phthalimide ring.

$R^1$ may preferably be a $C_1$-$C_3$ alkyl group, and more preferably a methyl group.

$R^2$ may preferably be a benzene ring which may be substituted, a thiophene ring which may be substituted, a benzisoxazole ring which may be substituted, a benzyl group which may be substituted, or a phenoxymethyl group which may be substituted.

The compounds represented by the aforementioned formula (I) may form a salt. Examples of the salt include, when an acidic group exists, salts of alkali metals and alkaline earth metals such as lithium, sodium, potassium, magnesium, and calcium; salts of ammonia and amines such as methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methylglucamine, and L-glucamine; or salts with basic amino acids such as lysine, δ-hydroxylysine, and arginine. When a basic group exists, examples include salts with mineral acids such as hydrochloric acid, hydrobromic acid, sulfuric acid, nitric acid, phosphoric acid; salts with organic acids such as methanesulfonic acid, benzenesulfonic acid, p-toluenesulfonic acid, acetic acid, propionic acid, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid, and salicylic acid; or salts with acidic amino acids such as aspartic acid, and glutamic acid.

In addition to the 3-substituted-4-pyrimidone derivatives represented by the aforementioned formula (I) and salts thereof, their solvates and hydrates also fall within the scope of the present invention. The 3-substituted-4-pyrimidone derivatives represented by the aforementioned formula (I) may have one or more asymmetric carbon atoms. As for the stereochemistry of such asymmetric carbon atoms, they may independently be in either (R) and (S) configuration, and the pyrimidone derivative may exist as stereoisomers such as optical isomers, or diastereoisomers. Any stereoisomers of pure form, any mixtures of stereoisomers, racemates and the like fall within the scope of the present invention Examples of preferred compounds of the present invention are shown in the table 1 set out below. However, the scope of the present invention is not limited by the following compounds.

TABLE 1

| Compound No. | STRUCTURE |
|---|---|
| A001 | 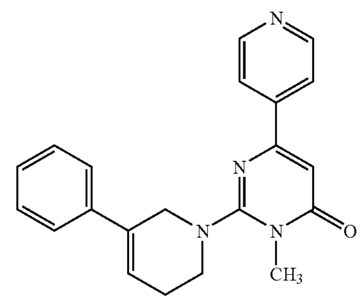 |
| A002 | 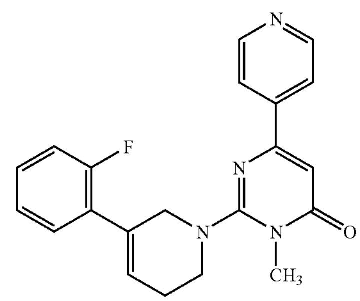 |
| A003 | 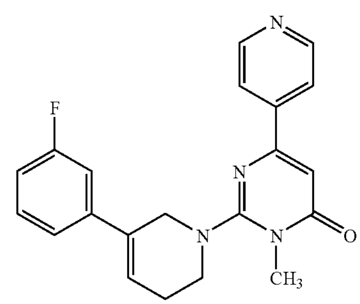 |
| A004 | 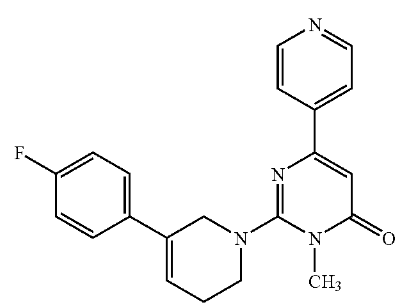 |

TABLE 1-continued
| Compound No. | STRUCTURE |
|---|---|
| A005 | 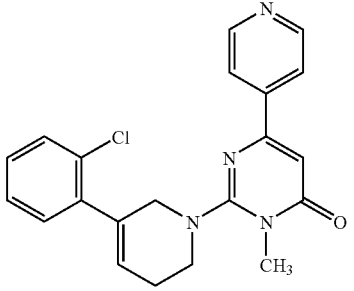 |
| A006 | 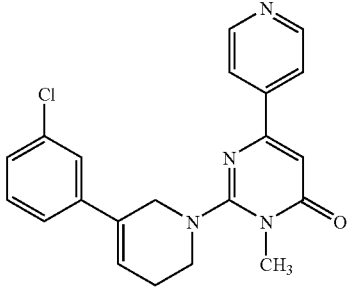 |
| A007 | 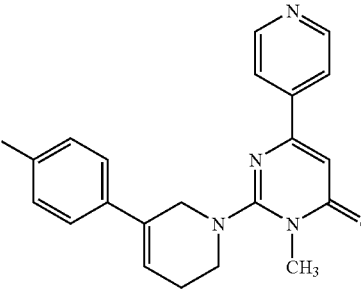 |
| A008 | 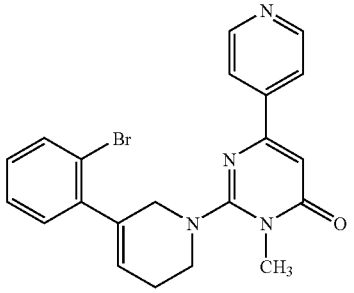 |
| A009 | 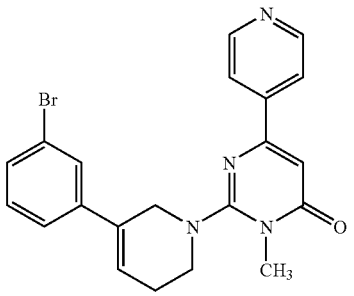 |
| A010 | 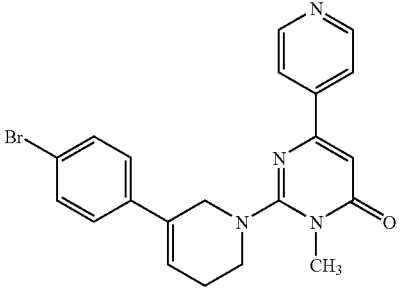 |
| A011 | 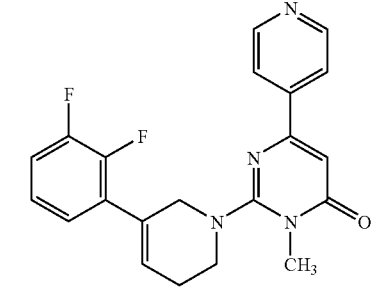 |
| A012 | 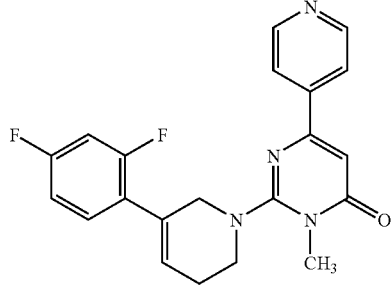 |
| A013 | 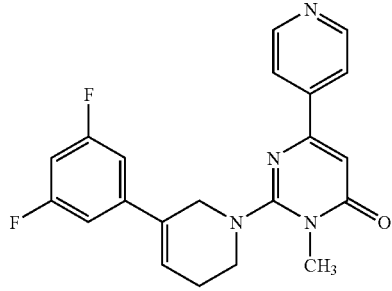 |
| A014 | 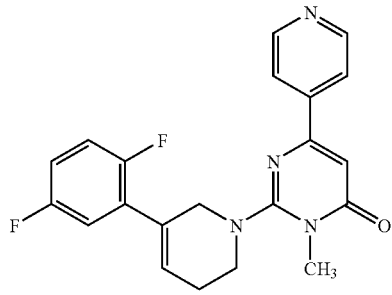 |

TABLE 1-continued

| Compound No. | STRUCTURE |
|---|---|
| A015 | (2,6-difluorophenyl derivative) |
| A016 | (2,3-dichlorophenyl derivative) |
| A017 | (2,4-dichlorophenyl derivative) |
| A018 | (2,5-dichlorophenyl derivative) |
| A019 | (2,6-dichlorophenyl derivative) |
| A020 | (2-methoxyphenyl derivative) |
| A021 | (3-methoxyphenyl derivative) |
| A022 | (4-methoxyphenyl derivative) |
| A023 | (2,3-dimethoxyphenyl derivative) |
| A024 | (2,4-dimethoxyphenyl derivative) |

TABLE 1-continued
| Compound No. | STRUCTURE |
|---|---|
| A025 | 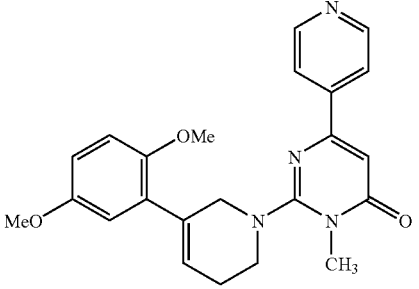 |
| A026 | 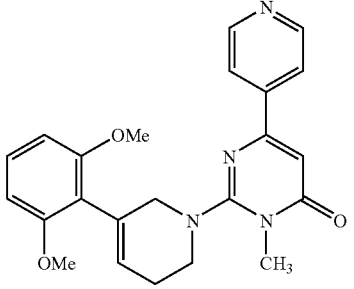 |
| A027 | 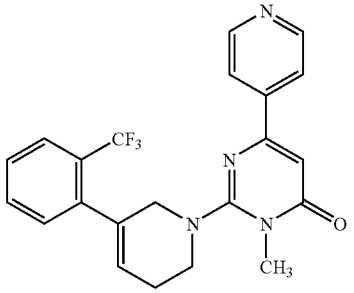 |
| A028 | 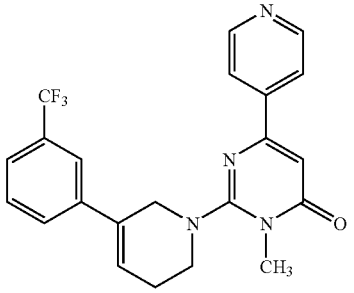 |
| A029 | 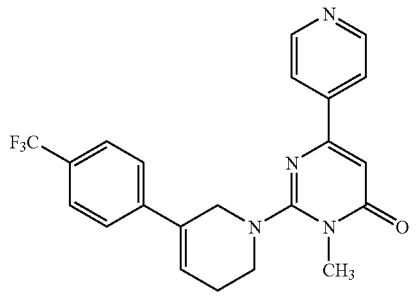 |
| A030 | 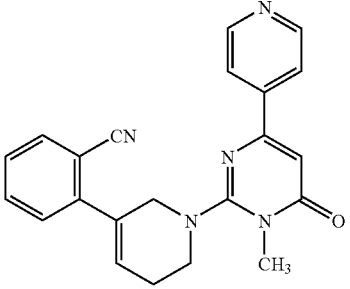 |
| A031 | 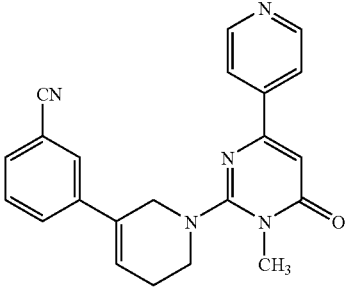 |
| A032 | 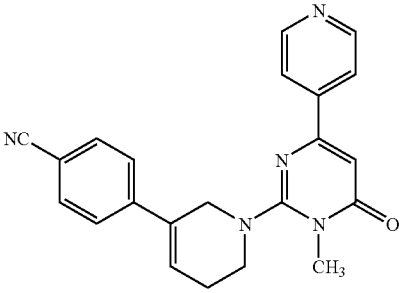 |
| A033 | 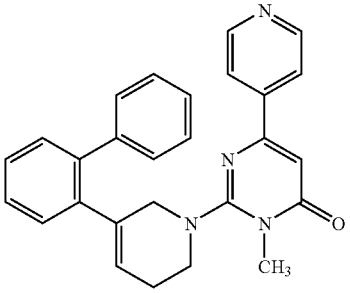 |
| A034 | 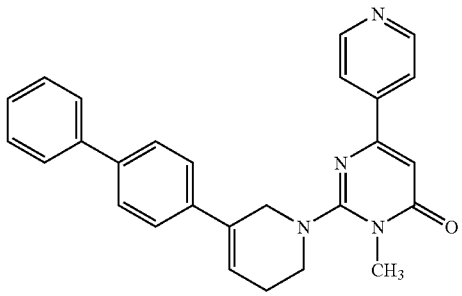 |

TABLE 1-continued

| Compound No. | STRUCTURE |
|---|---|
| A035 | 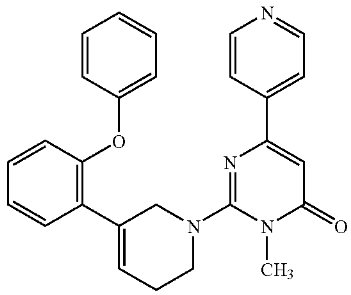 |
| A036 | 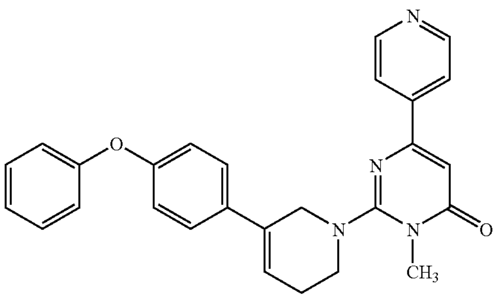 |
| A037 | 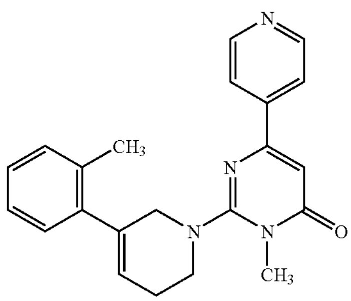 |
| A038 | 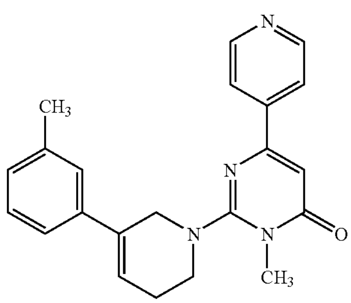 |
| A039 | 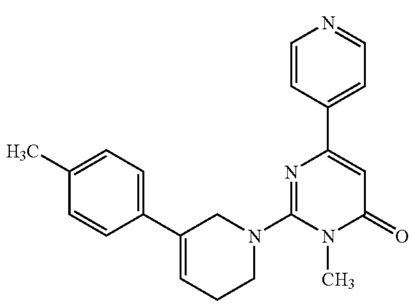 |
| A040 | |
| A041 | |
| A042 | |
| A043 | |
| A044 | |

TABLE 1-continued

| Compound No. | STRUCTURE |
|---|---|
| A045 | (structure) |
| A046 | (structure) |
| A047 | (structure) |
| A048 | (structure) |
| A049 | (structure) |
| A050 | (structure) |
| A051 | (structure) |
| A052 | (structure) |
| A053 | (structure) |
| A054 | (structure) |

TABLE 1-continued
| Compound No. | STRUCTURE |
|---|---|
| A055 | 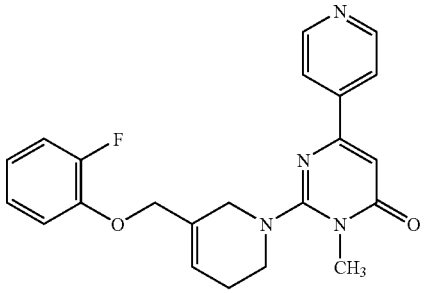 |
| A056 | 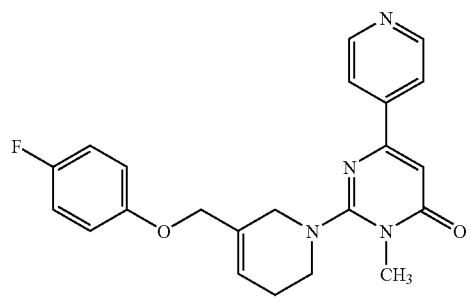 |
| A057 | 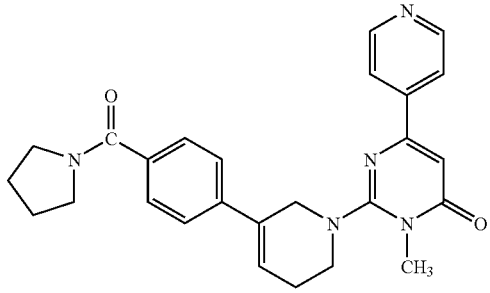 |
| A058 | |
| A059 | |
| A060 | |
| B001 | 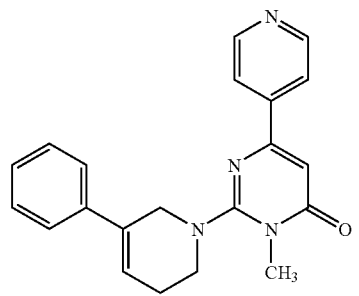 |油
TABLE 1-continued
| Compound No. | STRUCTURE |
|---|---|
| B002 | 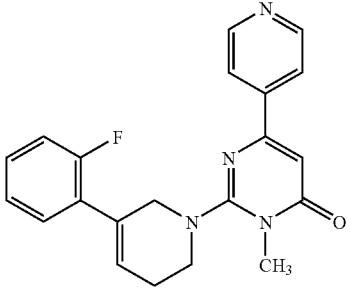 |
| B003 | 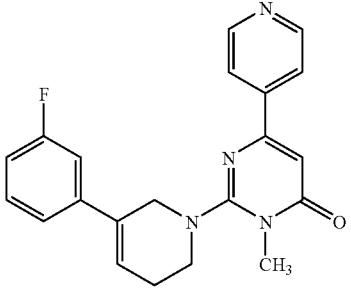 |
| B004 | 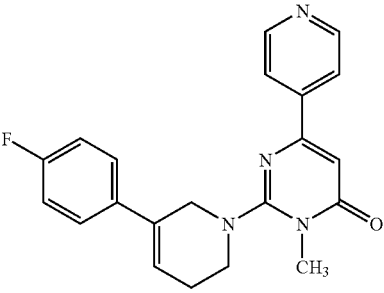 |
| B005 | 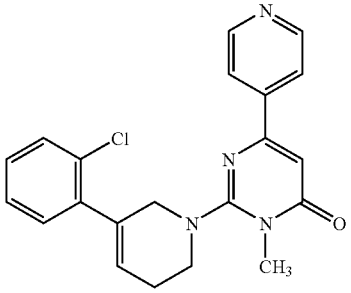 |
| B006 | 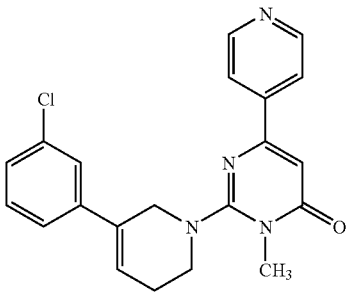 |

TABLE 1-continued
| Compound No. | STRUCTURE |
|---|---|
| B007 | 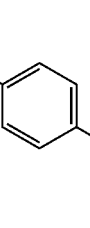 |
| B008 | 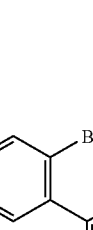 |
| B009 | 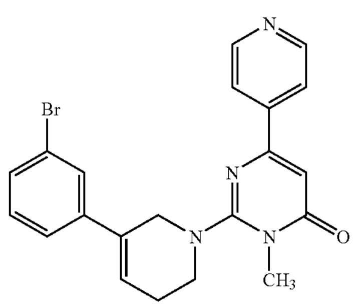 |
| B010 | 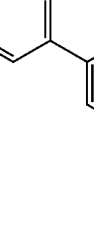 |
| B011 | 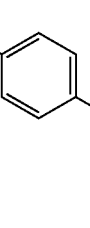 |
| B012 | 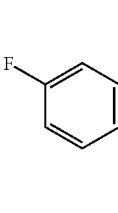 |
| B013 |  |
| B014 |  |
| B015 | 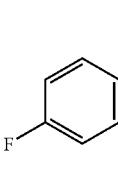 |
| B016 |  |

TABLE 1-continued
| Compound No. | STRUCTURE |
|---|---|
| B017 | 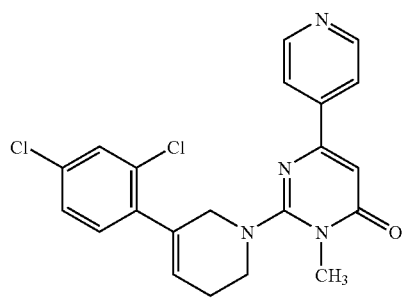 |
| B018 | 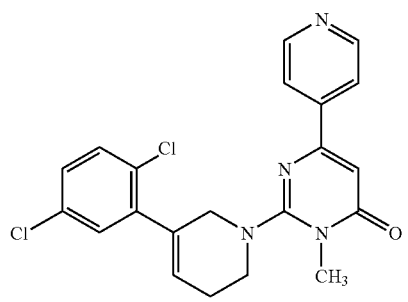 |
| B019 | 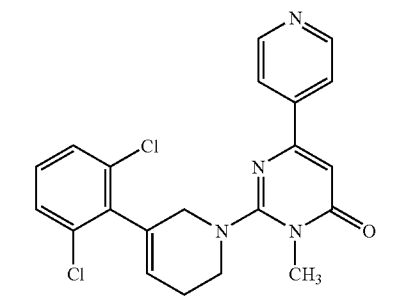 |
| B020 | 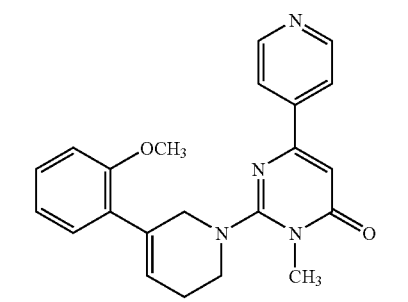 |
| B021 | 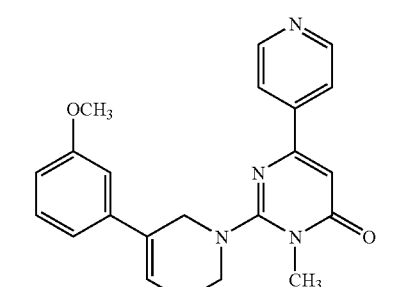 |
| B022 | 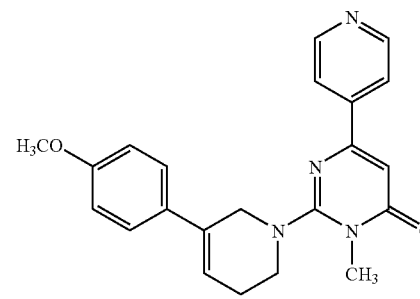 |
| B023 | 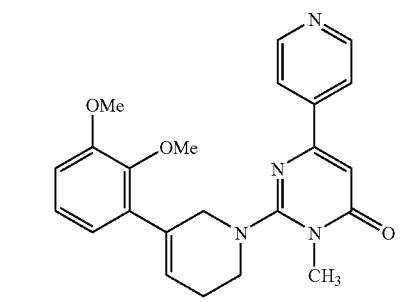 |
| B024 | 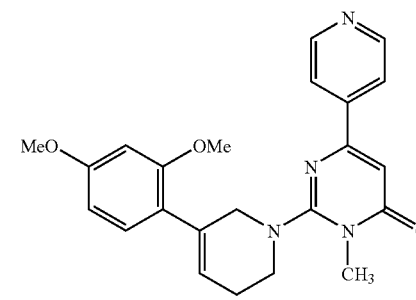 |
| B025 | 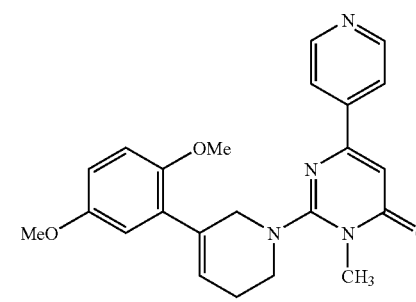 |
| B026 | 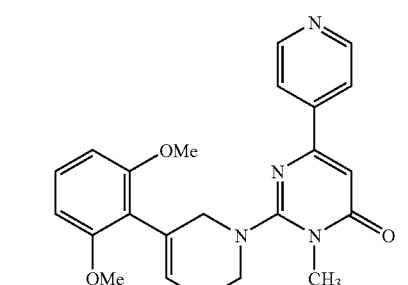 |

TABLE 1-continued

| Compound No. | STRUCTURE |
|---|---|
| B027 | (structure) |
| B028 | (structure) |
| B029 | (structure) |
| B030 | (structure) |
| B031 | (structure) |
| B032 | (structure) |
| B033 | (structure) |
| B034 | (structure) |
| B035 | (structure) |
| B036 | (structure) |

TABLE 1-continued
| Compound No. | STRUCTURE |
|---|---|
| B037 | 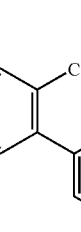 |
| B038 | 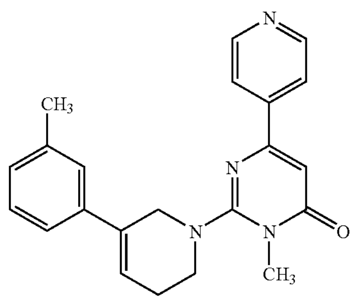 |
| B039 | 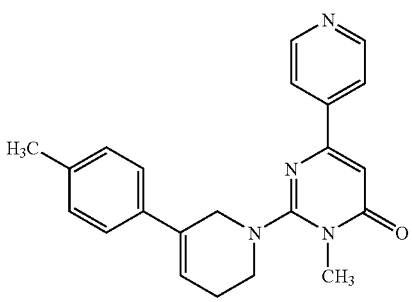 |
| B040 | 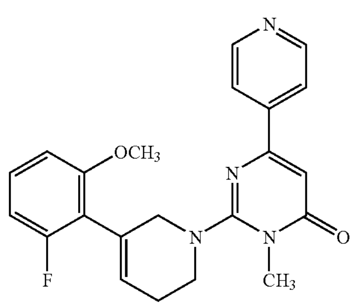 |
| B041 | 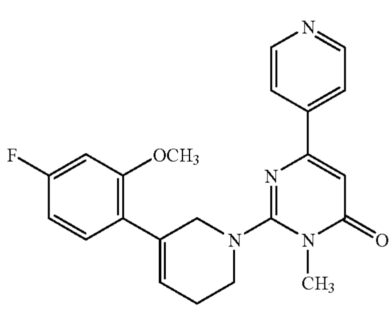 |
| B042 | 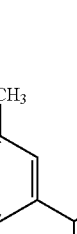 |
| B043 |  |
| B044 |  |
| B045 | 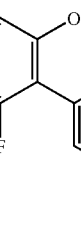 |
| B046 | |

TABLE 1-continued
| Compound No. | STRUCTURE |
|---|---|
| B047 | 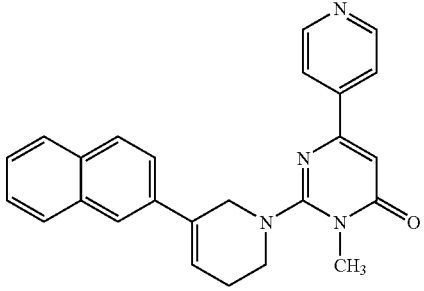 |
| B048 | 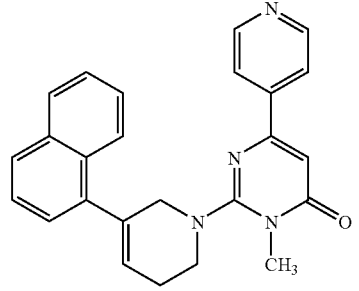 |
| B049 | 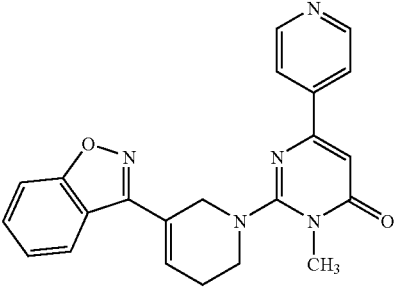 |
| B050 | 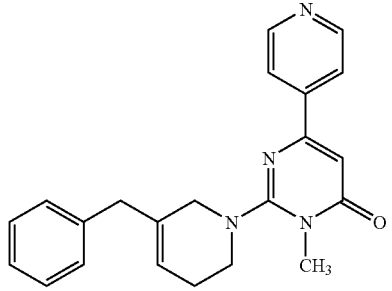 |
| B051 | 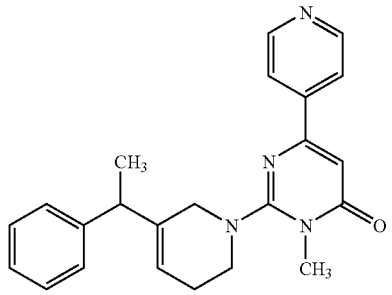 |
| B052 | 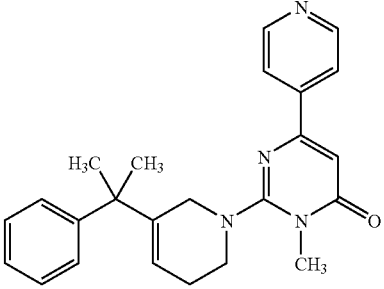 |
| B053 | 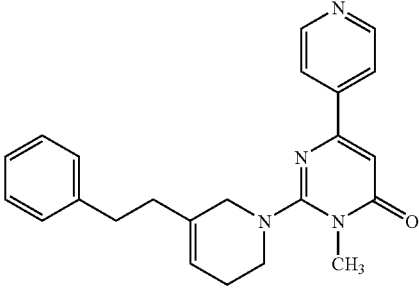 |
| B054 | 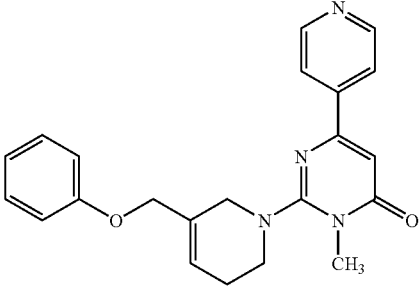 |
| B055 | 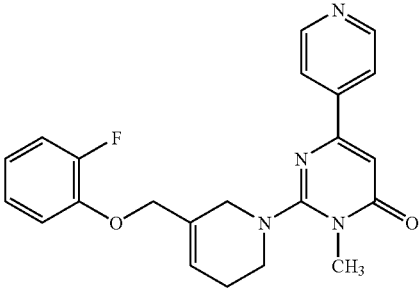 |
| B056 | 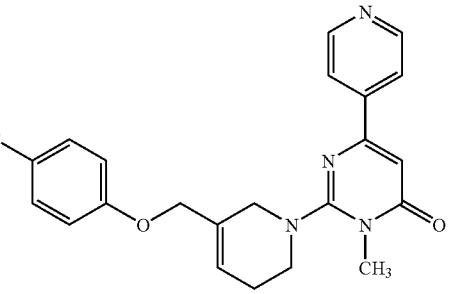 |

TABLE 1-continued

| Compound No. | STRUCTURE |
|---|---|
| B057 | ![structure] |
| B058 | |
| B059 | |
| B060 | |

Particularly preferred compounds of the present invention represented by formula (I) include:

A001: 2-(5-phenyl-3,6-dihydro-2H-pyridin-1-yl)-3-methyl-6-pyridin-4-yl-3H-pyrimidin-4-one;
A020: 2-[5-(2-methoxyphenyl)-3,6-dihydro-2H-pyridin-1-yl]-3-methyl-6-pyridin-4-yl-3H-pyrimidin-4-one;
A022: 2-[5-(4-methoxyphenyl)-3,6-dihydro-2H-pyridin-1-yl]-3-methyl-6-pyridin-4-yl-3H-pyrimidin-4-one;
A008: 2-[5-(2-bromophenyl)-3,6-dihydro-2H-pyridin-1-yl]-3-methyl-6-pyridin-4-yl-3H-pyrimidin-4-one;
A002: 2-[5-(2-fluorophenyl)-3,6-dihydro-2H-pyridin-1-yl]-3-methyl-6-pyridin-4-yl-3H-pyrimidin-4-one;
A004: 2-[5-(4-fluorophenyl)-3,6-dihydro-2H-pyridin-1-yl]-3-methyl-6-pyridin-4-yl-3H-pyrimidin-4-one;
A012: 2-[5-(2,4-difluorophenyl)-3,6-dihydro-2H-pyridin-1-yl]-3-methyl-6-pyridin-4-yl-3H-pyrimidin-4-one;
A005: 2-[5-(2-chlorophenyl)-3,6-dihydro-2H-pyridin-1-yl]-3-methyl-6-pyridin-4-yl-3H-pyrimidin-4-one;
A007: 2-[5-(4-chlorophenyl)-3,6-dihydro-2H-pyridin-1-yl]-3-methyl-6-pyridin-4-yl-3H-pyrimidin-4-one;
A017: 2-[5-(2,4-dichlorophenyl)-3,6-dihydro-2H-pyridin-1-yl]-3-methyl-6-pyridin-4-yl-3H-pyrimidin-4-one;
A026: 2-[5-(2,6-dimethoxyphenyl)-3,6-dihydro-2H-pyridin-1-yl]-3-methyl-6-pyridin-4-yl-3H-pyrimidin-4-one;
A027: 2-[5-(2-trifluoromethylphenyl)-3,6-dihydro-2H-pyridin-1-yl]-3-methyl-6-pyridin-4-yl-3H-pyrimidin-4-one;
A049: 2-[5-(benzisoxazole-3-yl)-3,6-dihydro-2H-pyridin-1-yl]-3-methyl-6-pyridin-4-yl-3H-pyrimidin-4-one;
A050: 2-(5-benzyl-3,6-dihydro-2H-pyridin-1-yl)-3-methyl-6-pyridin-4-yl-3H-pyrimidin-4-one;
A033: 2-(5-biphenyl-2-yl-3,6-dihydro-2H-pyridin-1-yl)-3-methyl-6-pyridin-4-yl-3H-pyrimidin-4-one;.
A043: 2-(5-thiophen-3-yl-3,6-dihydro-2H-pyridin-1-yl)-3-methyl-6-pyridin-4-yl-3H-pyrimidin-4-one;
A044: 2-(5-thiophen-2-yl-3,6-dihydro-2H-pyridin-1-yl)-3-methyl-6-pyridin-4-yl-3H-pyrimidin-4-one;
A056: 2-[5-(4-fluorophenoxymethyl)-3,6-dihydro-2H-pyridin-1-yl]-3-methyl-6-pyridin-4-yl-3H-pyrimidin-4-one; and
A057: 2-[5-(4-pyrrolidinylcarbonylphenyl)-3,6-dihydro-2H-pyridin-1-yl]-3-methyl-6-pyridin-4-yl-3H-pyrimidin-4-one;

B001: 2-(5-phenyl-3,6-dihydro-2H-pyridin-1-yl)-3-methyl-6-pyrimidin-4-yl-3H-pyrimidin-4-one;
B020: 2-[5-(2-methoxyphenyl)-3,6-dihydro-2H-pyridin-1-yl]-3-methyl-6-pyrimidin-4-yl-3H-pyrimidin-4-one;
B022: 2-[5-(4-methoxyphenyl)-3,6-dihydro-2H-pyridin-1-yl]-3-methyl-6-pyrimidin-4-yl-3H-pyrimidin-4-one;
B008: 2-[5-(2-bromophenyl)-3,6-dihydro-2H-pyridin-1-yl]-3-methyl-6-pyrimidin-4-yl-3H-pyrimidin-4-one;
B002: 2-[5-(2-fluorophenyl)-3,6-dihydro-2H-pyridin-1-yl]-3-methyl-6-pyrimidin-4-yl-3H-pyrimidin-4-one;
B004: 2-[5-(4-fluorophenyl)-3,6-dihydro-2H-pyridin-1-yl]-3-methyl-6-pyrimidin-4-yl-3H-pyrimidin-4-one;
B012: 2-[5-(2,4-difluorophenyl)-3,6-dihydro-2H-pyridin-1-yl]-3-methyl-6-pyrimidin-4-yl-3H-pyrimidin-4-one;
B005: 2-[5-(2-chlorophenyl)-3,6-dihydro-2H-pyridin-1-yl]-3-methyl-6-pyrimidin-4-yl-3H-pyrimidin-4-one;
B007: 2-[5-(4-chlorophenyl)-3,6-dihydro-2H-pyridin-1-yl]-3-methyl-6-pyrimidin-4-yl-3H-pyrimidin-4-one;
B017: 2-[5-(2,4-dichlorophenyl)-3,6-dihydro-2H-pyridin-1-yl]-3-methyl-6-pyrimidin-4-yl-3H-pyrimidin-4-one;
B026: 2-[5-(2,6-dimethoxyphenyl)-3,6-dihydro-2H-pyridin-1-yl]-3-methyl-6-pyrimidin-4-yl-3H-pyrimidin-4-one;
B027: 2-[5-(2-trifluoromethylphenyl)-3,6-dihydro-2H-pyridin-1-yl]-3-methyl-6-pyrimidin-4-yl-3H-pyrimidin-4-one;
B049: 2-[5-(benzisoxazole-3-yl)-3,6-dihydro-2H-pyridin-1-yl]-3-methyl-6-pyrimidin-4-yl-3H-pyrimidin-4-one;
B050: 2-(5-benzyl-3,6-dihydro-2H-pyridin-1-yl)-3-methyl-6-pyrimidin-4-yl-3H-pyrimidin-4-one;
B033: 2-(5-biphenyl-2-yl-3,6-dihydro-2H-pyridin-1-yl)-3-methyl-6-pyrimidin-4-yl-3H-pyrimidin-4-one;
B043: 2-(5-thiophen-3-yl-3,6-dihydro-2H-pyridin-1-yl)-3-methyl-6-pyrimidin-4-yl-3H-pyrimidin-4-one;
B044: 2-(5-thiophen-2-yl-3,6-dihydro-2H-pyridin-1-yl)-3-methyl-6-pyrimidin-4-yl-3H-pyrimidin-4-one;
B056: 2-[5-(4-fluorophenoxymethyl)-3,6-dihydro-2H-pyridin-1-yl]-3-methyl-6-pyrimidin-4-yl-3H-pyrimidin-4-one; and
B057: 2-[5-(4-pyrrolidinylcarbonylphenyl)-3,6-dihydro-2H-pyridin-1-yl]-3-methyl-6-pyrimidin-4-yl-3H-pyrimidin-4-one. Salts of the aforementioned preferred compound, and solvates or hydrates of the aforementioned compounds and salts thereof are also preferred.

The 3-substituted-4-pyrimidone compounds represented by the aforementioned formula (I) can be prepared, for example, according to the method explained below.

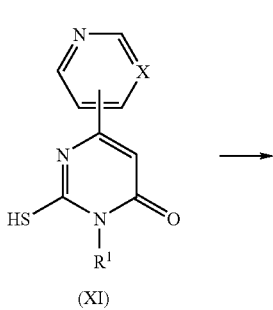

(XI)

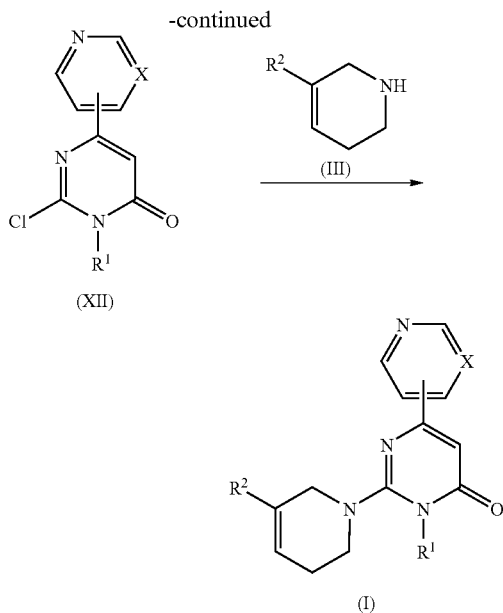

(In the above scheme, definitions of $R^1$ and $R^2$ are the same as those already described.)

The 2-mercaptopyrimidone represented by the above formula (XI) is prepared easily by a modification of the method described in EP 354,179. The reaction is carried out in the presence of a base such as sodium hydroxide, potassium hydroxide, sodium methoxide, sodium ethoxide, potassium t-butoxide, sodium carbonate, sodium hydrogencarbonate, potassium carbonate, triethylamine, diisopropylethylamine, and 1,8-diazabicyclo[5,4,0]undec-7-en for 1 to 100 hours at a suitable temperature ranging from 0° C. to 200° C. under nitrogen or argon atmosphere or under ordinary air to afford the desired compound (XI). Examples of a solvent for the reactions include, for example, alcoholic solvent such as methanol, ethanol, 1-propanol, isopropanol, tert-butanol, ethylene glycol, propylene glycol; etheric solvents such as diethyl ether, tert-butyl methyl ether, tetrahydrofuran, isopropyl ether; hydrocarbonic solvents such as benzene, toluene, xylene; halogenated hydrocarbonic solvents such as dichloromethane, chloroform, dichloroethane; aprotic polar solvents such as formamide, N,N-dimethylformamide, N,N-dimethylacetamide, N-methylpyrrolidone, dimethyl sulfoxide, sulfolane, hexamethylphosphoric triamide, water and the like. Generally, a single solvent or a mixture of two or more solvents may be used so as to be suitable to a base used.

Then the 2-mercaptopyrimidone derivative (XI) is transformed into the 2-chloropyrimidone (XII) by a chlorinating agent. The reaction time and temperature depend on the chlorinating agent used. Examples of a chlorinating agent for the reactions include, for example, thionyl chloride, thionyl chloride and dimethylformamide, phosphorus oxychloride, phosphorus oxychloride and dimethylformamide, oxalyl chloride, phosphorous oxychloride and dimethylformamide, and phosphorus pentachloride.

The chloride derivative (XII) is then allowed to react with the amine (III) or salts thereof in the presence of a base such as sodium hydroxide, potassium hydroxide, sodium methoxide, sodium ethoxide, sodium carbonate, sodium hydrogencarbonate, potassium carbonate, triethylamine, diisopropylethylamine, and 1,8-diazabicyclo[5,4,0]undec-7-en for 1 to 100 hours at a suitable temperature ranging from 0° C. to 200° C. under nitrogen or argon atmosphere or under ordinary air to afford the desired compound (I).

Examples of a solvent for the reactions include, for example, alcoholic solvent such as methanol, ethanol, 1-propanol, isopropanol, tert-butanol, ethylene glycol, propylene glycol; etheric solvents such as diethyl ether, tert-butyl methyl ether, tetrahydrofuran, isopropyl ether; hydrocarbonic solvents such as benzene, toluene, xylene; halogenated hydrocarbonic solvents such as dichloromethane, chloroform, dichloroethane; aprotic polar solvents such as formamide, N,N-dimethylformamide, N,N-dimethylacetamide, N-methylpyrrolidone, dimethyl sulfoxide, sulfolane, hexamethylphosphoric triamide, water and the like. Generally, a single solvent or a mixture of two or more solvents may be used so as to be suitable to a base used.

The compounds of the present invention have inhibitory activity against TPK1, and they inhibit TPK1 activity in neurodegenerative diseases such as Alzheimer disease, thereby suppress the neurotoxicity of Aβ and the formation of PHF and inhibit the nerve cell death. Accordingly, the compounds of the present invention are useful as an active ingredient of a medicament which radically enables preventive and/or therapeutic treatment of Alzheimer disease. In addition, the compounds of the present invention are also useful as an active ingredient of a medicament for preventive and/or therapeutic treatment of cerebrovascular accidents (e.g. ischemic, age-related macular degeneration), Down syndrome, cerebral bleeding due to cerebral amyloid angiopathy, Parkinson's disease, subacute sclerosing panencephalitic parkinsonism, postencephalitic parkinsonism, pugilistic encephalitis, Guam parkinsonism-dementia complex, Lewy body disease, tauopathies (e.g. Pick's disease, corticobasal degeneration, frontotemporal dementia, progressive supranuclear palsy), and other dementia including vascular dementia; acute and other traumatic injuries, brain and spinal cord trauma, peripheral neuropathies, retinopathies and glaucoma, as well as other diseases such as non-insulin dependent diabetes (such as diabetes type II), obesity, manic depressive illness, schizophrenia, alopecia, cancers such as breast cancer, non-small cell lung carcinoma, thyroid cancer, T or B-cell leukemia, and a virus-induced tumor.

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more of pharmaceutical additives. As the active ingredient of the medicament of the present invention, two or more of the aforementioned substance may be used in combination. The above pharmaceutical composition may be supplemented with an active ingredient of other medicament for the treatment of Alzheimer disease and the like.

A type of the pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline.

Sustained-release preparations such as those coated with a polymer may be directly administered intracerebrally.

Types of pharmaceutical additives used for the manufacture of the pharmaceutical composition, content rations of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administration, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

Dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

EXAMPLES

The present invention will be explained more specifically with reference to examples. However, the scope of the present invention is not limited to the following examples. The compound number in the examples corresponds to that in the table above.

Reference Example 1

Synthesis of 2-mercapto-3-methyl-6-pyridin-4-yl-3H-pyrimidin-4-one

A solution of ethyl 3-oxo-3-(4-pyridyl)propionate (29.0 g, 150 mmol), N-methyl thiourea (40.6 g, 450 mmol) and 1,8-diazabicyclo[5,4,0]-7-undecene (22.4 ml, 150 mmol) was refluxed for 4 hours and the solution of methanesulfonic acid (14.4 g, 150 mmol) in water (50 ml) was added after cooling by ice-water. The precipitate was washed with water, filtered and dried to give the title compound (23.7 g, 72%).

$^1$H-NMR (DMSO-$d_6$) δ: 3.58 (s, 3H), 6.40 (s, 1H), 7.72 (dd, J=1.8, 4.5 Hz, 2H), 8.73 (dd, J=1.5, 4.8 Hz, 2H), 12.92 (brd, 1H).

Reference Example 2

Synthesis of 2-chloro-3-methyl-6-pyridin-4-yl-3H-pyrimidin-4-one

Phosphorous oxychloride (26.11 g, 170 mmol) was added to dimethylformamide (180 ml) and stirred 20 min. 2-mercapto-3-methyl-6-(4-pyridyl)-pyrimidine-4-one (24.15 g, 110 mmol) was added to the solution and stirred 5 min and then stirred at 70° C. for 2 hours. Ethyl acetate (630 ml) was added to the ice-cooled solution and precipitate was collected by filtration after 20 minutes stirring. After drying, the precipitate was dissolved in water (400 ml) and pH was adjusted to 10 by aqueous sodium hydroxide. The precipitate was washed with water, filtered and dried to give the title compound (18.82 g, 77%).

$^1$H-NMR (CDCl$_3$) δ: 3.72 (s, 3H), 6.90 (s, 1H), 7.78 (dd, J=1.7, 4.5 Hz, 2H), 8.75 (dd, J=1.6, 4.5 Hz, 2H).

Reference Example 3

Synthesis of 2-mercapto-3-methyl-6-pyrimidin-4-yl-3H-pyrimidin-4-one

A solution of ethyl 3-oxo-3-(4-pyrimidyl)propionate (34.1 g, 176 mmol), N-methylthiourea (47.5 g, 527 mmol) and 1,8-diazabicyclo[5,4,0]-7-undecene (26.3 ml, 176 mmol) in ethanol (340 ml) was refluxed for 2 hours and the solution of methanesulfonic acid (16.9 g, 176 mmol) in water (70 ml) was added after cooling by ice-water. The precipitate was washed with water, filtered and dried to give the title compound (30.2 g, 78%).

$^1$H-NMR (DMSO-$d_6$) δ: 3.56 (s, 3H), 6.88 (s, 1H), 8.24 (dd, J=1.2, 5.4 Hz, 1H), 9.05 (d, J=5.4 Hz, 1H), 9.38 (s, 1H), 11.94 (s, 1H).

MS [M–H]$^-$: 219.

Reference Example 4

Synthesis of 2-chloro-3-methyl-6-pyrimidin-4-yl-3H-pyrimidin-4-one

Phosphorous oxychloride (4.60 g, 30 mmol) was added to dimethylformamide (32 ml) and stirred 20 min at 0° C. 2-Mercapto-3-methyl-6-pyrimidin-4-yl-pyrimidin-4-one (4.40 g, 20 mmol) was added to the solution and stirred 5 min and then stirred at 70° C. for 1 hour. The reaction mixture was poured into ice water, neutralized by solid K$_2$CO$_3$, and extracted with ethyl acetate. The organic layer was washed with brine, dried over Na$_2$SO$_4$ and evaporated in vacuo. Purification of the residue by silica gel column chromatography (ethyl acetate) gave the title compound (1.20 g, 27%).

$^1$H-NMR (CDCl$_3$) δ: 3.74 (s, 3H), 7.56 (s, 1H), 8.18 (d, J=5.1, 1H), 8.92 (d, J=5.1 Hz, 1H), 9.30 (s, 1H).

MS [M+H]$^+$: 223.

Example 1

Synthesis of 2-[5-(2-chlorophenyl)-3,6-dihydro-2H-pyridin-1-yl]-3-methyl-6-pyridin-4-yl-3H-pyrimidin-4-one: {3-methyl-2-[5-(2-chlorophenyl)-3,6-dihydro-pyridin-1(2H)-yl]-6-pyridin-4-ylpyrimidin-4(3H)-one} (Compound No. A005 in Table-1)

A mixture of 2-chlorophenylboronic acid (5.0 g), 3-bromopyridine (4.8 g) and tetrakis(triphenylphosphine)palladium(0) (1.0 g) in toluene (47 ml), aqueous 2 M sodium carbonate solution (35 ml) and ethanol (2.4 ml) was heated under reflux for 5.5 h. The reaction mixture was cooled, and the toluene layer was separated. The aqueous layer was extracted with ethyl acetate and the combined organic extracts were dried (MgSO$_4$), filtered, and the filtrate evaporated under reduced pressure to give crude 3-(2-chlorophenyl)pyridine (7.9 g). To a solution of the 3-(2-chlorophenyl) pyridine (7.9 g) in dichloromethane (50 ml) was added iodomethane (3.8 ml) and the mixture was stirred for 15 h. The solvent was evaporated under reduced pressure and the obtained residue was crystallized from ethyl acetate to give a pale-yellow crystal. To a solution of the obtained crystals in methanol (60 ml) was added sodium borohydride (1.7 g) under ice-cooling, and the mixture was stirred at room temperature for 3 h. The mixture was quenched with a saturated aqueous sodium chloride solution. The mixture was extracted with ethyl acetate. The extract was washed with a saturated aqueous sodium chloride solution, and dried over anhydrous magnesium sulfate. The solvent was evaporated under reduced pressure to give a crude 5-(2-chlorophenyl)-1,2,3,6-tetrahydro-1-methylpyridine (5.9 g).

To a solution of the 5-(2-chlorophenyl)-1,2,3,6-tetrahydro-1-methylpyridine (5.9 g) in dichloromethane (60 ml) was added 1-chloroethyl chloroformate (5.1 ml) and the mixture was stirred for 2.5 h. The mixture was washed with water and then with a saturated aqueous sodium chloride solution, and dried over anhydrous magnesium sulfate, and the solvent was evaporated under reduced pressure to give brown oil. A solution of the obtained oil in methanol was refluxed for 2 h. The solvent was evaporated under reduced pressure and the obtained residue was crystallized from ethyl acetate to give 5-(2-chlorophenyl)-1,2,3,6-tetrahydropyridine hydrochloride (2.4 g). A solution of 5-(2-chlorophenyl)-1,2,3,6-tetrahydropyridine hydrochloride (156 mg), 2-chloro-1,6-dihydro-1-methyl-6-oxo-4-(pyridin-4-yl)pyrimidine (150 mg) and triethylamine (236 μl) in dimethylformamide (3 ml) was stirred at room temperature for 6 h. To the reaction mixture was added water (3 ml), and the precipitated crystals were collected by filtration to give the title compound (240 mg) as white crystals.

$^1$H-NMR (CDCl$_3$) δ: 2.56 (m, 2H), 3.53 (m, 2H), 3.55 (s, 3H), 4.10 (s, 2H), 5.88 (m, 1H), 6.65 (s, 1H), 7.20-7.27 (m, 3H), 7.39 (m, 1H), 7.83 (d, J=5.2 Hz, 2H), 8.67 (d, J=5.2 Hz, 2H)

MS: 378 (M+)

Example 2

Synthesis of 2-[5-(2,6-dimethoxyphenyl)-3,6-dihydro-2H-pyridin-1-yl]-3-methyl-6-pyridin-4-yl-3H-pyrimidin-4-one: {3-methyl-2-[5-(2,6-dimethoxyphenyl)-3,6-dihydropyridin-1(2H)-yl]-6-pyridin-4-ylpyrimidin-4(3H)-one} (Compound No. A026 in Table-1)

5-(2,6-dimethoxyphenyl)-1,2,3,6-tetrahydropyridine hydrochloride was prepared from 2,6-dimethoxyphenylboronic acid in the same manner as in Example 1.

A solution of 5-(2,6-dimethoxyphenyl)-1,2,3,6-tetrahydropyridine hydrochloride (173 mg), 2-chloro-1,6-dihydro-1-methyl-6-oxo-4-(pyridin-4-yl)pyrimidine (150 mg) and triethylamine (236 μl) in dimethylformamide (5 ml) was stirred at room temperature for 2 h. To the reaction mixture was added water (5 ml), and the precipitated crystals were collected by filtration to give the title compound (250 mg) as white crystals.

$^1$H-NMR (CDCl$_3$) δ: 2.57 (m, 2H), 3.53 (s, 3H), 3.58 (m, 2H), 3.75 (s, 6H), 3.93 (m, 2H), 5.74 (m, 1H), 6.55-6.61 (m, 3H), 7.21 (m, 1H), 7.81 (d, J=6.4 Hz, 2H), 8.67 (d, J=6.0 Hz, 2H)

MS: 404 (M+)

Example 3

Synthesis of 2-[5-(2-chlorophenyl)-3,6-dihydro-2H-pyridin-1-yl]-3-methyl-6-pyrimidin-4-yl-3H-pyrimidin-4-one: {3-methyl-2-[5-(2-chlorophenyl)-3,6-dihydropyridin-1(2H)-yl]-6-pyrimidin-4-ylpyrimidin-4(3H)-one} (Compound No. B005 in Table-1)

A mixture of 2-chlorophenylboronic acid (5.0 g), 3-bromopyridine (4.8 g) and tetrakis(triphenylphosphine)palladium(0) (1.0 g) in toluene (47 ml), aqueous 2 M sodium carbonate solution (35 ml) and ethanol (2.4 ml) was heated under reflux for 5.5 h. The reaction mixture was cooled, and the toluene layer was separated. The aqueous layer was extracted with ethyl acetate and the combined organic extracts were dried (MgSO$_4$), filtered, and the filtrate evaporated under reduced pressure to give crude 3-(2-chlorophenyl)pyridine (7.9 g). To a solution of the 3-(2-chlorophenyl) pyridine (7.9 g) in dichloromethane (50 ml) was added iodomethane (3.8 ml) and the mixture was stirred for 15 h. The solvent was evaporated under reduced pressure and the obtained residue was crystallized from ethyl acetate to give a pale-yellow crystal. To a solution of the obtained crystals in methanol (60 ml) was added sodium borohydride (1.7 g) under ice-cooling, and the mixture was stirred at room temperature for 3 h. The mixture was quenched with a saturated aqueous sodium chloride solution. The mixture was extracted with ethyl acetate. The extract was washed with a saturated aqueous sodium chloride solution, and dried over anhydrous magnesium sulfate. The solvent was evaporated under reduced pressure to give a crude 5-(2-chlorophenyl)-1,2,3,6-tetrahydro-1-methylpyridine (5.9 g).

To a solution of the 5-(2-chlorophenyl)-1,2,3,6-tetrahydro-1-methylpyridine (5.9 g) in dichloromethane (60 ml) was added 1-chloroethyl chloroformate (5.1 ml) and the mixture was stirred for 2.5 h. The mixture was washed with water and a saturated aqueous sodium chloride solution, and dried over anhydrous magnesium sulfate and the solvent was evaporated under reduced pressure to give brown oil. A solution of the obtained oil in methanol was refluxed for 2 h. The solvent was evaporated under reduced pressure and the obtained residue was crystallized from ethyl acetate to give 5-(2-chlorophenyl)-1,2,3,6-tetrahydropyridine hydrochloride (2.4 g). A solution of 5-(2-chlorophenyl)-1,2,3,6-tetrahydropyridine hydrochloride (155 mg), 2-chloro-1,6-dihydro-1-methyl-6-oxo-4-(pyrimidin-4-yl)pyrimidine (150 mg) and triethylamine (235 μl) in dimethylformamide (3 ml) was stirred at room temperature for 2 h. To the reaction mixture was added water (3 ml), and the precipitated crystals were collected by filtration to give the title compound (240 mg) as white crystals.

$^1$H-NMR (CDCl$_3$) δ: 2.56 (m, 2H), 3.52 (m, 2H), 3.56 (s, 3H), 4.09 (m, 2H), 5.88 (m, 1H), 7.21-7.29 (m, 4H), 7.39 (m, 1H), 8.13 (d, J=5.1 Hz, 1H), 8.82 (d, J=5.1 Hz, 1H), 9.25 (s, 1H)

MS: 379 (M+)

Example 4

Synthesis of 2-[5-(2,6-dimethoxyphenyl)-3,6-dihydro-2H-pyridin-1-yl]-3-methyl-6-pyrimidin-4-yl-3H-pyrimidin-4-one: {3-methyl-2-[5-(2,6-dimethoxyphenyl)-3,6-dihydropyridin-1(2H)-yl]-6-pyrimidin-4-ylpyrimidin-4(3H)-one} (Compound No. B026 in Table-1)

5-(2,6-dimethoxyphenyl)-1,2,3,6-tetrahydropyridine hydrochloride was prepared from 2,6-dimethoxyphenylboronic acid in the same manner as in Example 1. A solution of 5-(2,6-dimethoxyphenyl)-1,2,3,6-tetrahydropyridine hydrochloride (172 mg), 2-chloro-1,6-dihydro-1-methyl-6-oxo-4-(pyrimidin-4-yl)pyrimidine (150 mg) and triethylamine (235 μl) in dimethylformamide (6 ml) was stirred at room temperature for 3 h. To the reaction mixture was added water (10 ml), and the precipitated crystals were collected by filtration to give the title compound (260 mg) as white crystals.

$^1$H-NMR (CDCl$_3$) δ: 2.60 (m, 2H), 3.57-3.61 (m, 5H), 3.78 (s, 6H), 3.94 (m, 2H), 5.76 (m, 1H), 6.59 (d, J=8.5 Hz, 2H), 7.22-7.28 (m, 2H), 8.20 (d, J=5.4 Hz, 1H), 8.84 (d, J=5.4 Hz, 1H), 9.27 (s, 1H)

MS: 405 (M+)

The compounds in the following table 2 were prepared in the same manner as the methods described above. The compound numbers in the following table correspond to those shown in the above-described table 1 of preferred compounds.

TABLE 2

| Compound No. | $^1$H-NMR (Solvent) δ: | [M+H]+ |
|---|---|---|
| A001 | (CDCl$_3$)2.57(m, 2H), 3.50(m, 2H), 3.59(s, 3H), 4.26(m, 2H), 6.25(m, 1H), 6.68(s, 1H), 7.32-7.40(m, 5H), 7.82(d, J=6.0Hz, 2H), 8.72(d, J=6.0Hz, 2H) | 345 |
| A002 | (d$_6$-DMSO)2.4-2.6(m, 2H), 3.44(s, 3H), 3.51(m, 2H), 4.19(s, 2H), 6.14(bs, 1H), 6.82(s, 1H), 7.20-7.30(m, 2H), 7.31-7.50(m, 2H), 7.97(d, J=5.4Hz, 2H), 8.68(d, J=5.4Hz, 2H) | 363 |
| A004 | (CDCl$_3$)3.19(m, 2H), 3.63(s, 3H), 3.78(m, 2H), 4.55(s, 2H), 6.68(s, 1H), 7.25-7.31(m, 3H), 7.47(m, 2H), 7.82(d, J=6.0Hz, 2H), 8.74(d, J=6.0Hz, 2H) | 363 |
| A005 | (CDCl$_3$)2.56(m, 2H), 3.53(m, 2H), 3.55(s, 3H), 4.10(s, 2H), 5.88(m, 1H), 6.65(s, 1H), 7.20-7.27(m, 3H), 7.39(m, 1H), 7.83(d, J=5.2Hz, 2H), 8.67(d, J=5.2Hz, 2H) | 378(M+) |
| A008 | (CDCl$_3$)2.56(m, 2H), 3.52-3.56(m, 5H), 4.08(s, 2H), 5.85(m, 1H), 6.65(s, 1H), 7.16-7.32(m, 3H), 7.57(d, J=8.0Hz, 1H), 7.83(d, 2H), 8.68(m, 2H) | 424 |
| A012 | (CDCl$_3$)2.55(m, 2H), 3.51(m, 2H), 3.55(s, 3H), 4.14(s, 2H), 6.05(m, 1H), 6.66(s, 1H), 6.80-6.89(m, 2H), 7.21-7.27(m, 2H), 7.84(d, J=6.1Hz, 2H), 8.69(d, J=6.1Hz, 2H) | 380(M+) |
| A017 | (CDCl$_3$)2.55(m, 2H), 3.50-3.58(m, 5H), 4.06(m, 2H), 5.88(m, 1H), 6.65(s, 1H), 7.15(d, J=8.3Hz, 1H), 7.22-7.27(m, 1H), 7.41(d, J=2.0Hz, 1H), 7.83(m, 2H), 8.68(d, J=5.8Hz, 2H) | 414 |
| A020 | (CDCl$_3$)2.57(m, 2H), 3.57(s, 3H), 3.58(m, 2H), 3.82(s, 3H), 4.18(m, 2H), 5.92(m, 1H), 6.65(s, 1H), 6.89-6.98(m, 2H), 7.19(m, 1H), 7.30(m, 1H), 7.81(d, J=6.0Hz, 2H), 8.69(d, J=6.0Hz, 2H) | 375 |
| A022 | (d$_6$-DMSO)2.4-2.6(m, 2H), 3.47(s, 3H), 3.77(m, 2H), 4.26(s, 2H), 6.23(bs, 1H), 7.02(s, 1H), 6.94, 7.44(ABq, 4H, J=8.7Hz), 8.44(d, J=5.4Hz, 2H), 8.91(d, J=5.4Hz, 2H) | 375 |
| A026 | (CDCl$_3$)2.57(m, 2H), 3.53(s, 3H), 3.58(m, 2H), 3.75(s, 6H), 3.93(m, 2H), 5.74(m, 1H), 6.55-6.61(m, 3H), 7.21(m, 1H), 7.81(d, J=6.4Hz, 2H), 8.67(d, J=6.0Hz, 2H) | 404(M+) |
| A027 | (CDCl$_3$)2.53(m, 2H), 3.50(m, 2H), 3.54(s, 3H), 4.01(m, 2H), 5.82(m, 1H), 6.65(s, 1H), 7.29(d, J=7.6Hz, 1H), 7.42(m, 1H), 7.52(m, 1H), 7.68(d, J=7.8Hz, 1H), 7.83(d, J=6.1Hz, 2H), 8.67(d, J=6.1Hz, 2H) | 412(M+) |
| A033 | (CDCl$_3$)2.57(m, 2H), 3.02(s, 3H), 3.46-3.49(m, 4H), 6.00(m, 1H), 6.58(s, 1H), 7.22-7.38(m, 9H), 7.80(d, J=6.1Hz, 2H), 8.71(d, J=6.1Hz, 2H) | 420(M+) |
| A043 | (CDCl$_3$)2.55(m, 2H), 3.47(m, 2H), 3.56(s, 3H), 4.22(m, 2H), 6.28(m, 1H), 6.67(s, 1H), 7.16(d, J=1.7Hz, 1H), 7.17-7.27(m, 2H), 7.33(dd, J=2.9, 5.1Hz, 1H), 7.89(dd, J=1.5, 4.6Hz, 2H), 8.71(d, J=6.1Hz, 2H), | 350(M+) |
| A044 | (CDCl$_3$)2.54(m, 2H), 3.47(m, 2H), 3.56(s, 3H), 4.24(m, 2H), 6.29(m, 1H), 6.67(s, 1H), | 350(M+) |

TABLE 2-continued

| Compound No. | ¹H-NMR (Solvent) δ: | [M+H]+ |
|---|---|---|
| A049 | 7.00-7.02(m, 2H), 7.19(m, 1H), 7.85(dd, J=1.7, 4.6Hz, 2H), 8.70(d, J=6.1Hz, 2H), (d₆-DMSO)2.67(m, 2H), 3.45(s, 3H), 3.55(m, 2H), 4.42(s, 2H), 6.82(s, 1H), 7.13(s, 1H), 7.44(m, 1H), 7.68(m, 1H), 7.79(d, J=7.8Hz, 1H), 7.97(d, J=5.4Hz, 2H), 8.16(d, J=7.8Hz, 1H), 8.67(d, J=5.4Hz, 2H) | 385(M+) |
| A050 | (CDCl₃)2.40(bs, 2H), 3.31-3.49(m, 4H), 3.41(s, 3H), 3.72(d, J=1.5Hz, 2H), 5.68(bs, 1H), 6.62(s, 1H), 7.18-7.38(m, 5H), 7.77(d, J=6.0Hz), 8.70(d, J=6.0Hz) | 359 |
| A056 | (d₆-DMSO)2.39(bs, 2H), 3.2-3.5(m, 2H), 3.35(s, 3H), 3.98(bs, 2H), 4.54(s, 2H), 6.05(bs, 1H), 6.9-7.2(m, 4H), 8.44(d, J=6.5Hz), 8.93(d, J=6.5Hz) | 393 |
| A057 | (CDCl₃)1.80-2.10(4H, m), 2.50-2.65(2H, m), 3.48(4H, dd, J=6.3, 14.1Hz), 3.59(3H, m), 3.66(2H, t, J=6.6Hz), 4.26(2H, d, J=1.8Hz), 6.25-6.35(1H, m), 6.68(1H, s), 7.43(2H, d, J=8.4Hz), 7.55(2H, d, J=8.4Hz), 7.82(2H, d, J=1.5, 4.8Hz), 8.72(2H, dd, J=1.5, 4.5Hz) | 442 |
| B001 | (CDCl₃)2.55(m, 2H), 3.46(m, 2H), 3.57(s, 3H), 4.24(m, 2H), 6.22(m, 1H), 7.24-7.40(m, 6H), 8.15(d, J=5.1Hz, 1H), 8.85(d, J=5.1Hz, 1H), 9.26(s, 1H) | 346 |
| B002 | (CDCl₃)2.55(m, 2H), 3.51(m, 2H), 3.56(s, 3H), 4.18(m, 2H), 6.08(m, 1H), 7.05-7.15(m, 2H), 7.24-7.30(m, 3H), 8.15(d, J=5.1Hz, 1H), 8.83(d, J=5.1Hz, 1H), 9.25(s, 1H) | 363(M+) |
| B004 | (d₆-DMSO)2.48-2.50(m, 2H), 3.46-3.47(m, 5H), 4.25(m, 2H), 6.30(m, 1H), 6.98(s, 1H), 7.20(m, 2H), 7.55(m, 2H), 8.26(d, J=5.1Hz, 1H), 8.99(d, J=5.1Hz, 1H), 9.28(d, J=1.5Hz, 1H) | 363(M+) |
| B005 | (CDCl₃)2.56(m, 2H), 3.52(m, 2H), 3.56(s, 3H), 4.09(m, 2H), 5.88(m, 1H), 7.21-7.29(m, 4H), 7.39(m, 1H), 8.13(d, J=5.1Hz, 1H), 8.82(d, J=5.1Hz, 1H), 9.25(s, 1H) | 379(M+) |
| B008 | (CDCl₃)2.52(m, 2H), 3.48(m, 2H), 3.52(s, 3H), 4.03(m, 2H), 5.81(m, 1H), 7.11-7.28(m, 4H), 7.54(d, J=8.0Hz, 1H), 8.11(d, J=5.1Hz, 1H), 8.78(d, J=5.1Hz, 1H), 9.21(s, 1H) | 425 |
| B012 | (d₆-DMSO)2.48-2.50(m, 2H), 3.44(s, 3H), 3.50(m, 2H), 4.17(m, 2H), 6.11(m, 1H), 6.97(s, 1H), 7.11(m, 1H), 7.28(m, 1H), 7.49(m, 1H), 8.19(d, J=5.1Hz, 1H), 8.97(d, J=5.1Hz, 1H), 9.28(s, 1H) | 381(M+) |
| B017 | (CDCl₃)2.55(m, 2H), 3.49(m, 2H), 3.55(s, 3H), 4.05(m, 2H), 5.88(m, 1H), 7.16(d, J=8.5Hz, 1H), 7.23-7.25(m, 1H), 7.29(s, 1H), 8.12(d, J=5.1Hz, 1H), 8.82(d, J=5.1Hz, 1H), 9.25(s, 1H) | 415 |
| B022 | (CDCl₃)2.54(m, 2H), 3.45(m, 2H), 3.57(s, 3H), 3.82(s, 3H), 4.20(m, 2H), 6.13(m, 1H), 6.90(d, J=8.6Hz, 2H), 7.31(d, J=8.6Hz, 2H), 8.15(d, J=5.1Hz, 1H), 8.84(d, J=5.1Hz, 1H), 9.26(s, 1H) | 376 |
| B026 | (CDCl₃)2.60(m, 2H), 3.57-3.61(m, 5H), 3.78(s, 6H), 3.94(m, 2H), 5.76(m, 1H), 6.59(d, J=8.5Hz, 2H), 7.22-7.28(m, 2H), 8.20(d, J=5.4Hz, 1H), 8.84(d, J=5.4Hz, 1H), 9.27(s, 1H) | 405(M+) |
| B027 | (CDCl₃)2.54(m, 2H), 3.49(m, 2H), 3.55(s, 3H), 4.00(m, 2H), 5.83(m, 1H), 7.30(m, 1H), 7.43(m, 1H), 7.53(m, 1H), 7.69(d, J=8.0Hz, 1H), 8.14(m, 1H), 8.82(d, J=5.1Hz, 1H), 9.26(s, 1H) | 413(M+) |
| B033 | (d₆-DMSO)2.48-2.50(m, 2H), 3.03(s, 3H), 3.41(m, 2H), 3.57(m, 2H), 5.90(m, 1H), 6.90(s, 1H), 7.19-7.25(m, 3H), 7.30-7.41(m, 6H), 8.09(dd, J=1.4, 5.1Hz, 1H), 9.00(d, J=5.1Hz, 1H), 9.28(d, J=1.4Hz, 1H) | 421(M+) |
| B043 | (CDCl₃)2.55(m, 2H), 3.45(m, 2H), 3.57(s, 3H), 4.22(m, 2H), 6.28(m, 1H), 7.17(m, 1H), 7.23(m, 1H), 7.30-7.34(m, 2H), 8.16(d, J=5.4Hz, 1H), 8.86(d, J=5.4Hz, 1H), 9.27(s, 1H) | 351(M+) |
| B044 | (d₆DMSO)2.48-2.50(m, 2H), 3.46-3.49(m, 5H), 4.26(m, 2H), 6.28(m, 1H), 6.98(s, 1H), 7.06(dd, J=3.4, 5.1Hz, 1H), 7.21(d, J=3.4Hz, 1H), 7.43(d, J=5.1Hz, 1H), 8.27(d, J=5.1Hz, 1H), 9.00(d, J=5.1Hz, 1H), 9.29(s, 1H) | 351(M+) |

TABLE 2-continued

| Compound No. | $^1$H-NMR (Solvent) δ: | [M+H]+ |
|---|---|---|
| B049 | (d$_6$-DMSO)2.69(m, 2H), 3.47(s, 3H), 3.57(m, 2H), 4.44(m, 1H), 6.99(s, 1H), 7.15(m, 1H), 7.45(m, 1H), 7.67(m, 1H), 7.80(d, J=8.6 Hz, 1H), 8.17-8.22(m, 2H), 9.01(d, J=5.1Hz, 1H), 9.29(s, 1H) | 387 |
| B057 | (CDCl$_3$)1.80-2.10(4H, m), 2.55-2.65(2H, m), 3.47(4H, dd, J=5.4, 10.2Hz), 3.59(3H, m), 3.66(2H, t, J=6.9Hz), 4.25(2H, d, J=1.2Hz), 6.25-6.35(1H, m), 7.32(1H, s), 7.42(2H, d, J=8.4Hz), 7.55(2H, d, J=8.4Hz), 8.16(1H, dd, J=1.2, 5.1Hz), 8.87(1H, d, J=5.1Hz), 9.28(1H, s) | 443 |

Test Example

Inhibitory Activity of the Medicament of the Present Invention Against P-GS1 Phosphorylation by Bovine Cerebral TPK1

A mixture containing 100 mM MES-sodium hydroxide (pH 6.5), 1 mM magnesium acetate, 0.5 mM EGTA, 5 mM β-mercaptoethanol, 0.02% Tween 20, 10% glycerol, 12 μg/ml P-GS1, 41.7 μM [γ-$^{32}$P] ATP (68 kBq/ml), bovine cerebral TPK1 and a compound shown in Table (a final mixture contained 1.7% DMSO deriving from a solution of a test compound prepared in the presence of 10% DMSO) was used as a reaction system. The phosphorylation was started by adding ATP, and the reaction was conducted at 25° C. for 2 hours, and then stopped by adding 21% perchloric-acid on ice cooling. The reaction mixture was centrifuged at 12,000 rpm for 5 minutes and adsorbed on P81 paper (Whatmann), and then the paper was washed four times with 75 mM phosphoric acid, three times with water and once with acetone. The paper was dried, and the residual radioactivity was measured using a liquid scintillation counter. The results are shown in the table below. The test compound markedly inhibited the P-GS1 phosphorylation by TPK1. The results strongly suggest that the medicaments of the present invention inhibit the TPK1 activity, thereby suppress the Aβ neurotoxicity and the PHF formation, and that the medicaments of the present invention are effective for preventive and/or therapeutic treatment of Alzheimer disease and the above-mentioned diseases.

TABLE 3

| Compound No. | IC$_{50}$ (nM) |
|---|---|
| A001 | 7 |
| A002 | 1.2 |
| A004 | 13 |
| A012 | 17 |
| A020 | 5 |
| A022 | 8.7 |
| A026 | 16 |
| A027 | 31 |
| A050 | 8 |
| A056 | 27 |
| A057 | 24 |
| B001 | 6.5 |
| B002 | 1.1 |
| B004 | 6.3 |
| B005 | 0.38 |
| B012 | 3.9 |

TABLE 3-continued

| Compound No. | IC$_{50}$ (nM) |
|---|---|
| B017 | 5.6 |
| B022 | 7.7 |
| B026 | 2.4 |
| B027 | 2.6 |
| B033 | 17 |
| B043 | 17 |
| B044 | 9 |
| B049 | 5.1 |
| B057 | 6.8 |

Formulation Example (1) Tablets

The ingredients below were mixed by an ordinary method and compressed by using a conventional apparatus.

| | |
|---|---|
| Compound of Example 1 | 30 mg |
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| | |
|---|---|
| Compound of Example 1 | 30 mg |
| Olive oil | 300 mg |
| Lecithin | 20 mg |

INDUSTRIAL APPLICABILITY

The compounds of the present invention have TPK1 inhibitory activity and are useful as an active ingredient of a medicament for preventive and/or therapeutic treatment of diseases caused by abnormal advance of TPK1 such as neurodegenerative diseases (e.g. Alzheimer disease) and the above-mentioned diseases.

The invention claimed is:

1. A pyrimidone compound represented by formula (I) or a salt thereof:

$$\text{(I)}$$

wherein X represents CH or nitrogen atom;
$R^1$ represents a $C_1$-$C_{12}$ alkyl group which may be substituted;
$R^2$ represents a $C_1$-$C_8$ alkyl group which may be substituted, a benzene ring which may be substituted, a naphthalene ring which may be substituted, an indan ring which may be substituted, a tetrahydronaphthalene ring which may be substituted, or an optionally substituted heterocyclic ring having 1 to 4 hetero atoms selected from the group consisting of oxygen atom, sulfur atom, and nitrogen atom, and having 5 to 10 ring-constituting atoms in total.

2. The pyrimidone compound or the salt thereof according to claim 1, wherein $R^1$ is methyl group.

3. The pyrimidone compound or the salt thereof according to claim 1, wherein the heterocyclic ring at $R^2$ is a group selected from a furan ring, a benzofuran ring, a thiophene ring, a benzothiophene ring, a benzisoxazole ring, and a 1H-indazole ring.

4. A pyrimidone compound which is selected from:
2-(5-phenyl-3,6-dihydro-2H-pyridin-1-yl)-3-methyl-6-pyridin-4-yl-3H-pyrimidin-4-one;
2-[5-(2-methoxyphenyl)-3,6-dihydro-2H-pyridin-1-yl]-3-methyl-6-pyridin-4-yl-3H-pyrimidin-4-one; 2-[5-(4-methoxyphenyl)-3,6-dihydro-2H-pyridin-1-yl]-3-methyl-6-pyridin-4-yl-3H-pyrimidin-4-one;
2-[5-(2-bromophenyl)-3,6-dihydro-2H-pyridin-1-yl]-3-methyl-6-pyridin-4-yl-3H-pyrimidin-4-one;
2-[5-(2-fluorophenyl)-3,6-dihydro-2H-pyridin-1-yl]-3-methyl-6-pyridin-4-yl-3H-pyrimidin-4-one;
2-[5-(4-fluorophenyl)-3,6-dihydro-2H-pyridin-1-yl]-3-methyl-6-pyridin-4-yl-3H-pyrimidin-4-one;
2-[5-(2,4-difluorophenyl)-3,6-dihydro-2H-pyridin-1-yl]-3-methyl-6-pyridin-4-yl-3H-pyrimidin-4-one;
2-[5-(2-chlorophenyl)-3,6-dihydro-2H-pyridin-1-yl]-3-methyl-6-pyridin-4-yl-3H-pyrimidin-4-one;
2-[5-(4-chlorophenyl)-3,6-dihydro-2H-pyridin-1-yl]-3-methyl-6-pyridin-4-yl-3H-pyrimidin-4-one;
2-[5-(2,4-dichlorophenyl)-3,6-dihydro-2H-pyridin-1-yl]-3-methyl-6-pyridin-4-yl-3H-pyrimidin-4-one;
2-[5-(2,6-dimethoxyphenyl)-3,6-dihydro-2H-pyridin-1-yl]-3-methyl-6-pyridin-4-yl-3H-pyrimidin-4-one;
2-[5-(2-trifluoromethylphenyl)-3,6-dihydro-2H-pyridin-1-yl]-3-methyl-6-pyridin-4-yl-3H-pyrimidin-4-one;
2-[5-(benzisoxazole-3-yl)-3,6-dihydro-2H-pyridin-1-yl]-3-methyl-6-pyridin-4-yl-3H-pyrimidin-4-one;
2-(5-benzyl-3,6-dihydro-2H-pyridin-1-yl)-3-methyl-6-pyridin-4-yl-3H-pyrimidin-4-one;
2-(5-biphenyl-2-yl-3,6-dihydro-2H-pyridin-1-yl)-3-methyl-6-pyridin-4-yl-3H-pyrimidin-4-one;
2-(5-thiophen-3-yl-3,6-dihydro-2H-pyridin-1-yl)-3-methyl-6-pyridin-4-yl-3H-pyrimidin-4-one;
2-(5-thiophen-2-yl-3,6-dihydro-2H-pyridin-1-yl)-3-methyl-6-pyridin-4-yl-3H-pyrimidin-4-one;
2-[5-(4-fluorophenoxymethyl)-3,6-dihydro-2H-pyridin-1-yl]-3-methyl-6-pyridin-4-yl-3H-pyrimidin-4-one;
2-[5-(4-pyrrolidinylcarbonylphenyl)-3,6-dihydro-2H-pyridin-1-yl]-3-methyl-6-pyridin-4-yl-3H-pyrimidin-4-one;
2-(5-phenyl-3,6-dihydro-2H-pyridin-1-yl)-3-methyl-6-pyrimidin-4-yl-3H-pyrimidin-4-one;
2-[5-(2-methoxyphenyl)-3,6-dihydro-2H-pyridin-1-yl]-3-methyl-6-pyrimidin-4-yl-3H-pyrimidin-4-one;
2-[5-(4-methoxyphenyl)-3,6-dihydro-2H-pyridin-1-yl]-3-methyl-6-pyrimidin-4-yl-3H-pyrimidin-4-one;
2-[5-(2-bromophenyl)-3,6-dihydro-2H-pyridin-1-yl]-3-methyl-6-pyrimidin-4-yl-3H-pyrimidin-4-one;
2-[5-(2-fluorophenyl)-3,6-dihydro-2H-pyridin-1-yl]-3-methyl-6-pyrimidin-4-yl-3H-pyrimidin-4-one;
2-[5-(4-fluorophenyl)-3,6-dihydro-2H-pyridin-1-yl]-3-methyl-6-pyrimidin-4-yl-3H-pyrimidin-4-one;
2-[5-(2,4-difluorophenyl)-3,6-dihydro-2H-pyridin-1-yl]-3-methyl-6-pyrimidin-4-yl-3H-pyrimidin-4-one;
2-[5-(2-chlorophenyl)-3,6-dihydro-2H-pyridin-1-yl]-3-methyl-6-pyrimidin-4-yl-3H-pyrimidin-4-one;
2-[5-(4-chlorophenyl)-3,6-dihydro-2H-pyridin-1-yl]-3-methyl-6-pyrimidin-4-yl-3H-pyrimidin-4-one;
2-[5-(2,4-dichlorophenyl)-3,6-dihydro-2H-pyridin-1-yl]-3-methyl-6-pyrimidin-4-yl-3H-pyrimidin-4-one;
2-[5-(2,6-dimethoxyphenyl)-3,6-dihydro-2H-pyridin-1-yl]-3-methyl-6-pyrimidin-4-yl-3H-pyrimidin-4-one;
2-[5-(2-trifluoromethylphenyl)-3,6-dihydro-2H-pyridin-1-yl]-3-methyl-6-pyrimidin-4-yl-3H-pyrimidin-4-one;
2-[5-(benzisoxazole-3-yl)-3,6-dihydro-2H-pyridin-1-yl]-3-methyl-6-pyrimidin-4-yl-3H-pyrimidin-4-one;
2-(5-benzyl-3,6-dihydro-2H-pyridin-1-yl)-3-methyl-6-pyrimidin-4-yl-3H-pyrimidin-4-one;
2-(5-biphenyl-2-yl-3,6-dihydro-2H-pyridin-1-yl)-3-methyl-6-pyrimidin-4-yl-3H-pyrimidin-4-one;
2-(5-thiophen-3-yl-3,6-dihydro-2H-pyridin-1-yl)-3-methyl-6-pyrimidin-4-yl-3H-pyrimidin-4-one;
2-(5-thiophen-2-yl-3,6-dihydro-2H-pyridin-1-yl)-3-methyl-6-pyrimidin-4-yl-3H-pyrimidin-4-one;
2-[5-(4-fluorophenoxymethyl)-3,6-dihydro-2H-pyridin-1-yl]-3-methyl-6-pyrimidin-4-yl-3H-pyrimidin-4-one;
2-[5-(4-pyrrolidinylcarbonylphenyl)-3,6-dihydro-2H-pyridin-1-yl]-3-methyl-6-pyrimidin-4-yl-3H-pyrimidin-4-one;
and salts thereof.

5. A medicament composition comprising as an active ingredient a substance selected from the pyrimidone compound represented by formula (I) or a salt thereof according to claim 1 and a pharmaceutical excipient.

6. A method for treating of Alzheimer Disease, comprising:
administering the medicament composition according to claim 5 to a patient in need thereof.

7. A method for treating of rheumatoid arthritis, comprising:
administering the medicament composition according to claim 5 to a patient in need thereof.

* * * * *